United States Patent
Okuda

(10) Patent No.: US 11,704,801 B2
(45) Date of Patent: Jul. 18, 2023

(54) METHODS AND SYSTEMS FOR ANALYZING BRAIN LESIONS WITH LONGITUDINAL 3D MRI DATA

(71) Applicant: The Board of Regents of the University of Texas System, Austin, TX (US)

(72) Inventor: Darin T Okuda, Coppell, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 244 days.

(21) Appl. No.: 17/031,010

(22) Filed: Sep. 24, 2020

(65) Prior Publication Data

US 2021/0090259 A1    Mar. 25, 2021

Related U.S. Application Data

(60) Provisional application No. 62/905,079, filed on Sep. 24, 2019.

(51) Int. Cl.
*G06K 9/00*    (2022.01)
*G06T 7/00*    (2017.01)
(Continued)

(52) U.S. Cl.
CPC .......... *G06T 7/0016* (2013.01); *A61B 5/0042* (2013.01); *A61B 5/055* (2013.01);
(Continued)

(58) Field of Classification Search
CPC ................................................. G06T 7/0016
See application file for complete search history.

(56) References Cited

U.S. PATENT DOCUMENTS 10,743,837 B2 *  8/2020  Sandhu ............... A61B 8/0825
11,093,787 B2    8/2021  Okuda et al.
(Continued)

FOREIGN PATENT DOCUMENTS

WO    WO 2018/005939    1/2018
WO    WO 2019/165464    8/2019

OTHER PUBLICATIONS

Absinta et al., "Association of Chronic Active Multiple Sclerosis Lesions With Disability In Vivo." *JAMA Neurol* 2019, 76(12):1474-1483.

(Continued)

*Primary Examiner* — Oneal R Mistry
(74) *Attorney, Agent, or Firm* — Norton Rose Fulbright US LLP

(57) ABSTRACT

Some methods of analyzing one or more brain lesions of a patient comprise, for each of the lesion(s), calculating one or more lesion characteristics from a first 3-dimensional (3D) representation of the lesion obtained from data taken at a first time and a second 3D representation of the lesion obtained from data taken at a second time that is after the first time. The characteristic(s) can include a change, form the first time to the second time, in the lesion's volume and/or surface area, the lesion's displacement from the first time to the second time, and/or the lesion's theoretical radius ratio at each of the first and second times. Some methods comprise characterizing whether the patient has multiple sclerosis and/or the progression of multiple sclerosis in the patient based at least in part on the calculation of the lesion characteristic(s) of each of the lesion(s).

21 Claims, 22 Drawing Sheets

(51) Int. Cl.
 A61B 5/00 (2006.01)
 A61B 5/055 (2006.01)
(52) U.S. Cl.
 CPC ....... A61B 5/7267 (2013.01); A61B 2576/026 (2013.01); G06T 2207/10088 (2013.01); G06T 2207/30016 (2013.01); G06T 2207/30096 (2013.01)

(56) References Cited

U.S. PATENT DOCUMENTS

| | | | | |
|---|---|---|---|---|
| 2004/0236217 | A1* | 11/2004 | Gerwin | A61B 5/416 |
| | | | | 600/437 |
| 2011/0255761 | A1* | 10/2011 | O'Dell | G06T 7/0014 |
| | | | | 382/128 |
| 2014/0270451 | A1* | 9/2014 | Zach | A61B 5/055 |
| | | | | 382/131 |
| 2015/0119697 | A1* | 4/2015 | Penn | G16H 50/20 |
| | | | | 600/420 |
| 2016/0109539 | A1* | 4/2016 | Mardor | G16H 40/63 |
| | | | | 600/420 |
| 2017/0256056 | A1* | 9/2017 | Jain | G06T 7/62 |
| 2018/0127507 | A1 | 5/2018 | Greenberg et al. | |
| 2019/0197347 | A1 | 6/2019 | Okuda et al. | |
| 2019/0248885 | A1 | 6/2019 | Liddelow et al. | |
| 2020/0005461 | A1* | 1/2020 | Yip | A61B 5/725 |
| 2020/0147065 | A1* | 5/2020 | Moraitis | A61P 35/00 |
| 2021/0041518 | A1 | 2/2021 | Okuda et al. | |
| 2021/0374459 | A1 | 12/2021 | Okuda et al. | |

OTHER PUBLICATIONS

Absinta et al., "Identification of Chronic Active Multiple Sclerosis Lesions on 3T MRI." AJNR Am J Neuroradiol 2018;39:1233-1238.
Brown et al., "Do Cerebral Small Vessel Disease and Multiple Sclerosis Share Common Mechanisms of White Matter Injury?" Stroke 2019, 50(8), 1968-1972 . . . .
Cannistraro et al., "CNS small vessel disease: A clinical review." Neurology 2019; 92:1146-1156.
Dal-Bianco et al., "Slow expansion of multiple sclerosis iron rim lesions: pathology and 7 T magnetic resonance imaging." Acta Neuropathol 2017;133, 25-42.
Dufouil et al., "Longitudinal study of blood pressure and white matter hyperintensities: the EVA MRI Cohort." Neurology 2001;56:921-926.
Elliott et al., "Slowly expanding/evolving lesions as a magnetic resonance imaging marker of chronic active multiple sclerosis lesions." Mult Scler 2019, 25(14), 1915-1925.
Fernando et al., "White matter lesions in an unselected cohort of the elderly: molecular pathology suggests origin from chronic hypoperfusion injury." Stroke 2006;37:1391-1398.
Frischer et al., "Clinical and pathological insights into the dynamic nature of the white matter multiple sclerosis plaque." Ann Neurol 2015;78:710-721.
Gouw et al., "Progression of white matter hyperintensities and incidence of new lacunes over a 3-year period: the Leukoaraiosis and Disability study." Stroke 2008;39:1414-1420.
Hammond et al. "Quantitative in vivo magnetic resonance imaging of multiple sclerosis at 7 Tesla with sensitivity to iron." Ann Neurol 2008;64:707-713.

Hansen et al. "Post-gadolinium 3-dimensional spatial, surface, and structural characteristics of glioblastomas differentiate pseudoprogression from true tumor progression." J Neurooncol 2018, 139, 731-738.
Hoogeveen et al., "MRI evaluation of the relationship between carotid artery endothelial shear stress and brain white matter lesions in migraine." J Cereb Blood Flow Metab 2019, 40(5), 1040-1047.
Lassmann et al., "Remyelination in multiple sclerosis." Mult Scler 1997;3:133-136.
Neuropathology Group. Medical Research Council Cognitive F, Aging S. Pathological correlates of late-onset dementia in a multicentre, community-based population in England and Wales. Neuropathology Group of the Medical Research Council Cognitive Function and Ageing Study (MRC CFAS). Lancet 2001;357:169-175.
Newton et al. "Three-Dimensional Shape and Surface Features Distinguish Multiple Sclerosis Lesions from Nonspecific White Matter Disease." J Neuroimaging 2017;27:613-619.
Okuda et al. "Incidental MRI anomalies suggestive of multiple sclerosis: the radiologically isolated syndrome." Neurology 2009;72:800-805.
Sachdev et al., "Progression of white matter hyperintensities in elderly individuals over 3 years." Neurology 2007;68:214-222.
Sati et al. "The central vein sign and its clinical evaluation for the diagnosis of multiple sclerosis: a consensus statement from the North American Imaging in Multiple Sclerosis Cooperative." Nat Rev Neurol 2016;12:714-722.
Schmidt et al., "Austrian Stroke Prevention S. Progression of cerebral white matter lesions: 6-year results of the Austrian Stroke Prevention Study." Lancet 2003;361:2046-2048.
Sethi et al., "Slowly eroding lesions in multiple sclerosis". Mult Scler 2017;23:464-472.
Sivakolundu et al., "Three-Dimensional Lesion Phenotyping and Physiologic Characterization Inform Remyelination Ability in Multiple Sclerosis." J Neuroimaging 2019, 29(5), 605-614.
Solomon et al., "Misdiagnosis of multiple sclerosis: Impact of the 2017 McDonald criteria on clinical practice." Neurology 2019;92:26-33.
Solomon et al., "The contemporary spectrum of multiple sclerosis misdiagnosis: A multicenter study." Neurology 2016;87:1393-1399.
Tallantyre et al. "Ultra-high-field imaging distinguishes MS lesions from asymptomatic white matter lesions." Neurology 2011;76:534-539.
Thompson et al., "Diagnosis of multiple sclerosis: 2017 revisions of the McDonald criteria." Lancet Neurol 2018; 17:162-173.
Van Veluw et al., "Different microvascular alterations underlie microbleeds and microinfarcts." Ann Neurol 2019;86:279-292.
Wardlaw et al., "Small vessel disease: mechanisms and clinical implications." Lancet Neurol 2019;18:684-696.
Ziemssen et al., "Optimizing treatment success in multiple sclerosis." J Neurol 2016;263:1053-1065.
International Search Report issued in corresponding International Application No. PCT/US2020/052452 dated Dec. 17, 2020.
International Preliminary Report on Patentability issued in corresponding International Application No. PCT/US2020/052452 dated Dec. 17, 2020.
Wang et al., "Classification of multiple sclerosis and non-specific white matter lesions using spherical harmonics descriptors." Proceedings of the 3rd International Workshop on Interactive and Spatial Computing (IWISC '18), Association for Computing Machinery, pp. 97-102, 2018.

* cited by examiner

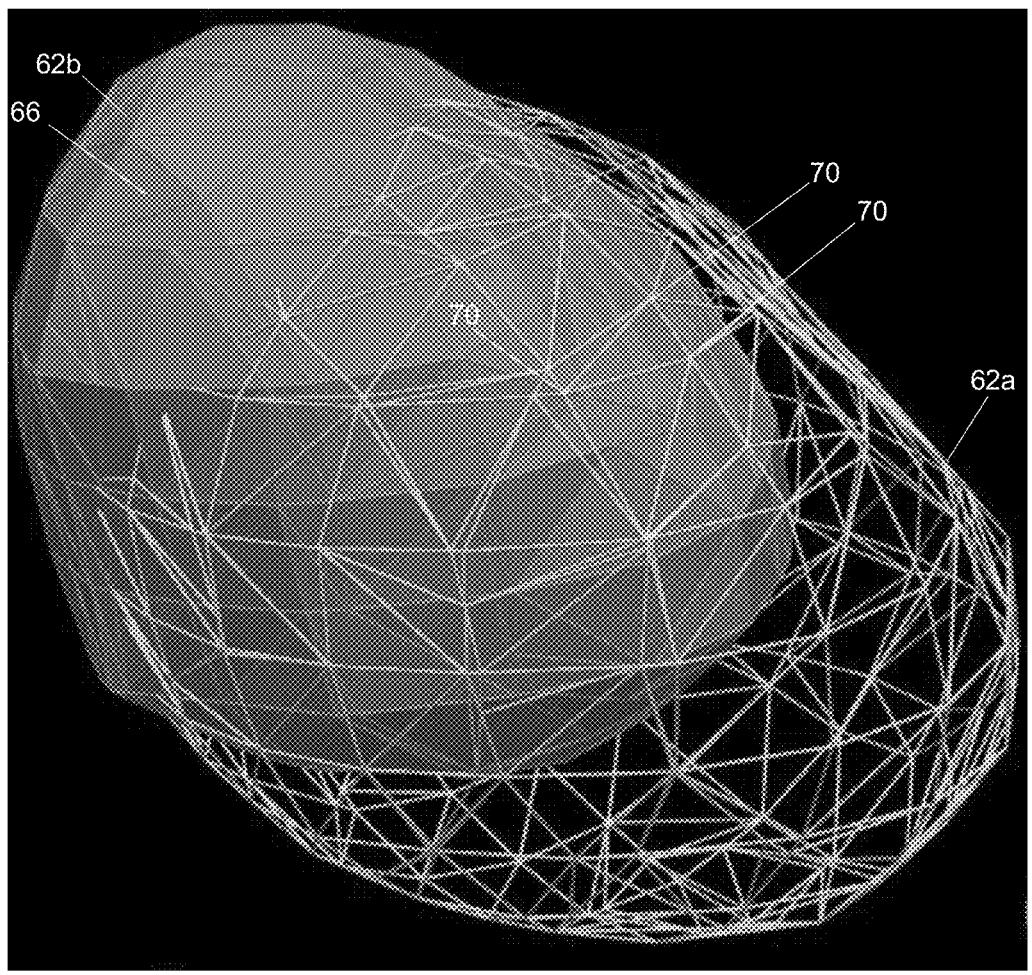
FIG. 4A
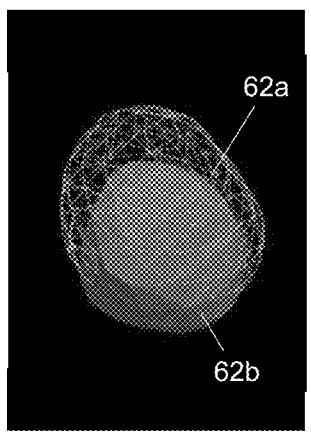 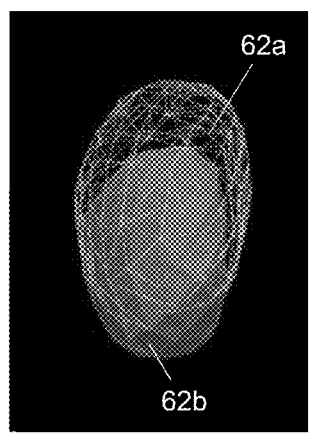 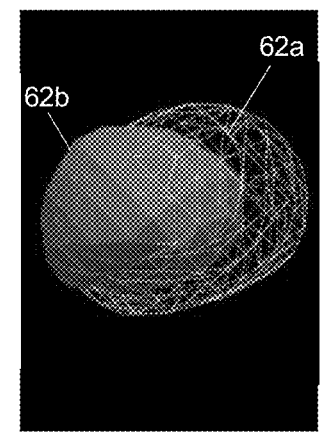
FIG. 4B  FIG. 4C  FIG. 4D

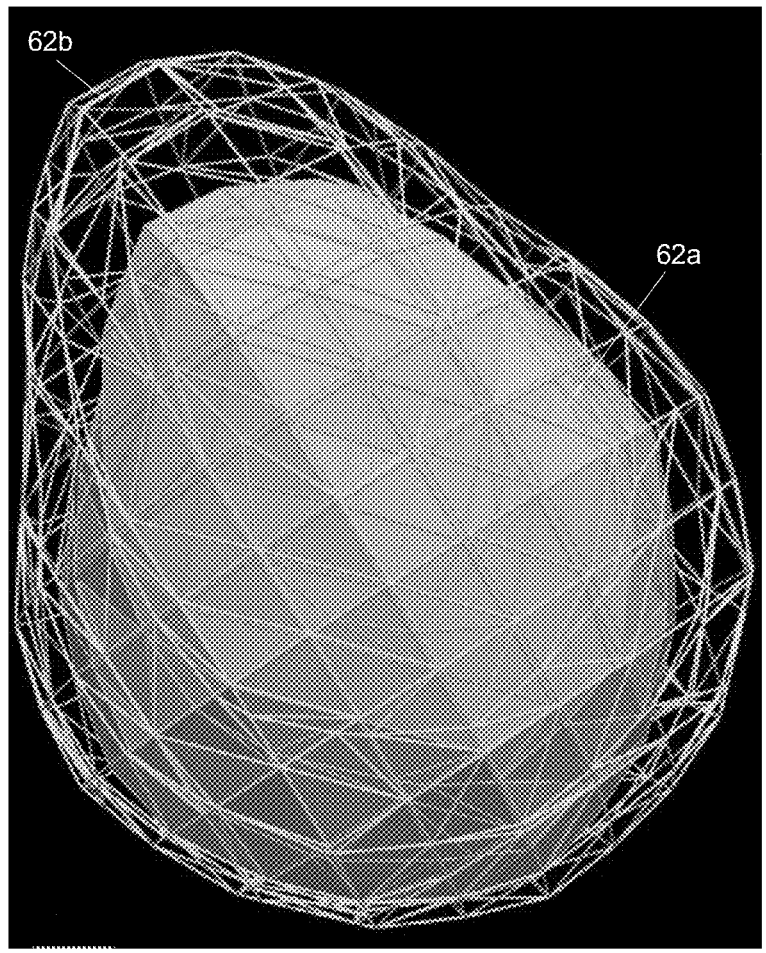
FIG. 9A
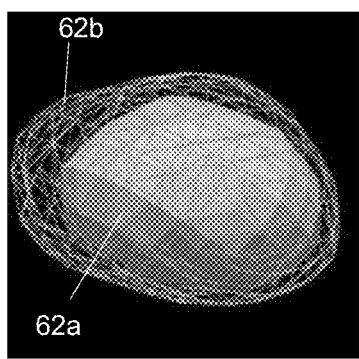 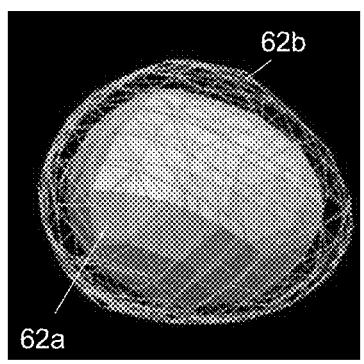 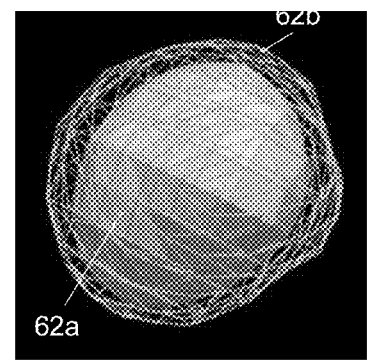
FIG. 9B  FIG. 9C  FIG. 9D

METHODS AND SYSTEMS FOR ANALYZING BRAIN LESIONS WITH LONGITUDINAL 3D MRI DATA

CROSS-REFERENCE TO RELATED APPLICATION

This application claims priority to U.S. Provisional Patent Application No. 62/905,079, filed Sep. 24, 2019, the entire contents of which are incorporated herein by reference.

FIELD OF INVENTION

The present invention relates generally to diagnosing and assessing the progression of multiple sclerosis in patients based on the analysis of brain lesions.

BACKGROUND

The diagnosis of multiple sclerosis (MS) is based on both clinical and radiological assessments of damage disseminated in both time and space. This may include a radiological assessment of whether a requisite number of lesions in the periventricular, juxtacortical, infratentorial, and spinal cord regions have a specific character (e.g., size, shape, and morphology) and spatial distribution patterns indicative of MS. The effective application of the existing dissemination in space criteria may be hindered by the highly sensitive nature of magnetic resonance imaging (MRI) technology, the heterogeneity of lesions resulting from a variety of medical conditions, concomitant radiological features resulting from age-related changes and disease, and the lack of additional radiological characteristics beyond two-dimensional (2D) descriptions.

Currently, MS diagnosis is typically performed using 2D MRI images. The implementation of certain imaging metrics, including the use of quantitative phase imaging, has improved lesion specificity. This may highlight the presence of central vasculature within lesions and distinct peripheral rings, suggesting the presence of iron within macrophages. The use of fluid-attenuated inversion recovery (FLAIR) MRI at 3 Tesla (T) and T2-weighted and susceptibility weighted imaging (SWI) at 7 T in larger patient groups has also been utilized to better characterize MS from non-MS lesions. However, this technique has been limited by the lack of appreciation of the central vessel in all orthogonal planes of view and the abundance of vessels intersecting lesions within the supratentorial region. Beyond these efforts, peripheral regions of hypointensity, presumed to be related to the presence of iron within macrophages, have also been described in MS patients.

Due to the shortcomings of the current 2D MRI, anomalies associated with non-specific white matter disease (NSWMD) may often be misinterpreted as MS lesions, resulting in the misclassification of patients even when coupled with clinical and para-clinical assessments. Accordingly, there is a need in the art for assessments that can more accurately characterize MS and NSWMD patients.

SUMMARY

Some of the present methods and systems address this need in the art through the use of multiple 3-dimensional (3D) representations of brain lesions obtained at different points in time. Changes in the lesion's volume, surface area, displacement, and/or shape over time can be assessed by comparing the 3D representations; the use of 3D representations permits meaningful detection and quantification of the changes, something that 2D MRI images—even those having a high resolution—typically cannot provide due to the limitations thereof. The changes in these parameters tend to be different for lesions associated with MS compared to those associated with NSWMD. For example, as compared to NSWMD lesions, MS lesions generally experience changes in volume and in surface area that are smaller and displacements that are larger. Further, NSWMD lesions tend to maintain a more spherical shape over time as compared to MS lesions. An assessment of criteria based on these temporal changes may better be able to distinguish MS and NSWD lesions compared to cross-sectional assessments that analyze lesions at only one point in time, yielding more accurate characterizations of the patient's disease state. In this manner, the use of 3D representations in conjunction with a temporal analysis can yield a more accurate characterization of MS and NSWMD compared to conventional techniques.

Some of the present methods of analyzing one or more lesions of a brain of a patient comprise, for each of the lesion(s), calculating one or more lesion characteristics from a first 3D representation of the lesion obtained from data taken at a first time and a second 3D representation of the lesion obtained from data taken at a second time that is after the first time. Some methods comprise characterizing whether the patient has multiple sclerosis and/or the progression of multiple sclerosis in the patient based at least in part on the calculation of the lesion characteristic(s) of each of the lesion(s). Some methods comprise, for each of the lesion(s), assessing whether one or more criteria are satisfied, wherein characterizing whether the patient has multiple sclerosis and/or the progression of multiple sclerosis in the patient is based at least in part on the assessment of the one or more criteria for each of the lesion(s).

Some of the present systems comprise one or more processors configured to, for each of the lesion(s), calculate one or more lesion characteristics from a first 3D representation of the lesion obtained from data taken at a first time and a second 3D representation of the lesion obtained from data taken at a second time that is after the first time. The processor(s), in some systems, are configured to characterize whether the patient has multiple sclerosis and/or the progression of multiple sclerosis in the patient based at least in part on the calculation of the lesion characteristic(s) of each of the lesion(s). In some systems, the processor(s) are configured to, for each of the lesion(s), assess whether one or more criteria are satisfied and characterize whether the patient has multiple sclerosis and/or the progression of multiple sclerosis in the patient based at least in part on the assessment of the one or more criteria for each of the lesion(s).

In some embodiments, the one or more lesion characteristics include a change, from the first time to the second time, in the volume of the lesion; a change, from the first time to the second time, in the surface area of the lesion; a displacement of the lesion from the first time to the second time; and/or the theoretical radius ratio of the lesion at each of the first and second times. The one or more criteria, for some embodiments, include a volume-based criterion that is satisfied when the change in volume of the lesion is less than or equal to a threshold volume change; an area-based criterion that is satisfied when the change in the surface area of the lesion is less than or equal to a threshold surface area change; a displacement-based criterion that is satisfied when the change in the position of the lesion is greater than or equal to a threshold displacement; and/or a deformation-based criterion that is satisfied when the theoretical radius ratio of the lesion at each of the first and second times is greater than or equal to a threshold theoretical radius ratio.

Some methods comprise determining the threshold volume change and/or the threshold surface area change based at least in part on the age of the patient, and in some systems the processor(s) are configured to determine the threshold volume change and/or the threshold area change based at least in part on the age of the patient. In some embodiments, the threshold volume change is less than or equal to 2.0 millimeters (mm), optionally less than or equal to 0.0 mm and/or the threshold surface area change is less than or equal to 1.5 mm, optionally less than or equal to 0.0 mm. In some methods, the threshold displacement and/or the threshold theoretical radius ratio are not determined based on the age of the patient, and in some systems the processor(s) are configured to assess whether the displacement-based criterion and/or the deformation-based criterion are satisfied without determining the threshold displacement and/or the threshold theoretical radius ratio based on the age of the patient. The threshold theoretical radius ratio, in some embodiments, is greater than or equal to 1.025, optionally greater than or equal to 1.02505.

In some embodiments, the data taken at the first time and the data taken at the second time each is a 3D MRI image of the brain of the patient. The time elapsed between the first and second times, in some embodiments, is between 6 months and 4 years.

Some methods comprise determining for at least a majority of the lesion(s) that at least one of the one or more criteria is satisfied and determining that the patient has multiple sclerosis.

The terms "a" and "an" are defined as one or more unless this disclosure explicitly requires otherwise. The terms "substantially" and "about" each is defined as largely but not necessarily wholly what is specified—and includes what is specified; e.g., substantially or about 90 degrees includes 90 degrees and substantially or about parallel includes parallel—as understood by a person of ordinary skill in the art. In any disclosed embodiment, the terms "substantially" and "about" may each be substituted with "within [a percentage] of" what is specified, where the percentage includes 0.1, 1, 5, and 10 percent.

The terms "comprise" and any form thereof such as "comprises" and "comprising," "have" and any form thereof such as "has" and "having," and "include" and any form thereof such as "includes" and "including" are open-ended linking verbs. As a result, an apparatus that "comprises," "has," or "includes" one or more elements possesses those one or more elements, but is not limited to possessing only those elements. Likewise, a method that "comprises," "has," or "includes" one or more steps possesses those one or more steps, but is not limited to possessing only those one or more steps.

Any embodiment of any of the apparatuses, systems, and methods can consist of or consist essentially of—rather than comprise/include/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Further, a device or system that is configured in a certain way is configured in at least that way, but it can also be configured in other ways than those specifically described.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIGS. 4A-4D each shows first and second 3D representations of one of the lesions of FIGS. 3A and 3B, the first 3D representation (empty mesh) representing the lesion at the first time and the second 3D representation (filled mesh) representing the lesion at the second time.

FIG. 7 also shows, for each of the lesions of the brain, a first 3D representation of the lesion taken at a first time (empty mesh) and a second 3D representation of the lesion taken at a second time (filled mesh) that is approximately 1 year after the first time.

FIGS. 9A-9D each shows first and second 3D representations of the lesion in FIGS. 8A and 8B, the first representation (filled mesh) representing the lesion at the first time and the second representation (empty mesh) representing the lesion at the second time.

DETAILED DESCRIPTION

Figure 1:
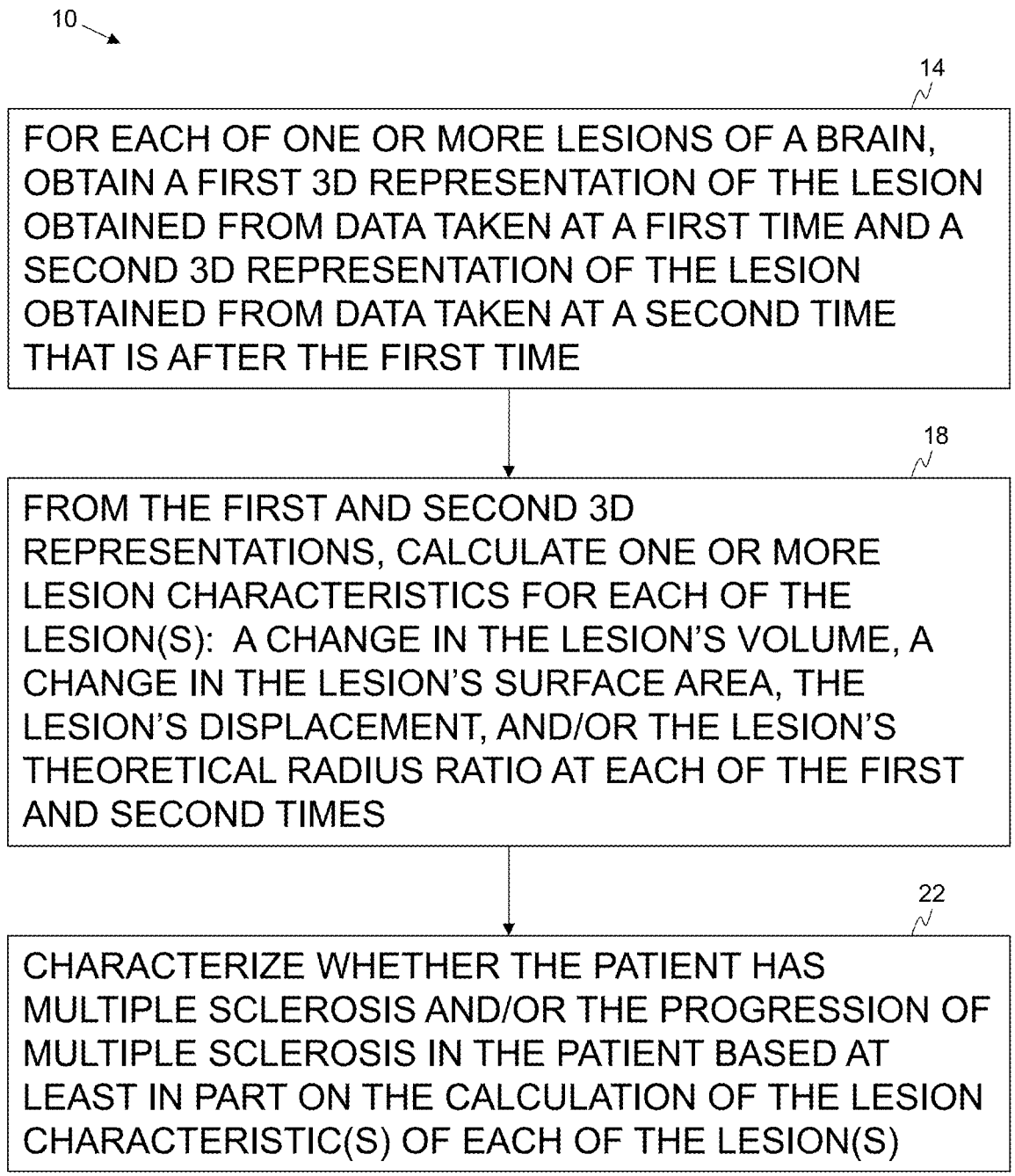
FIG. 1 illustrates some of the present methods of analyzing one or more lesions of a brain using 3D MRI.
Figure 2:
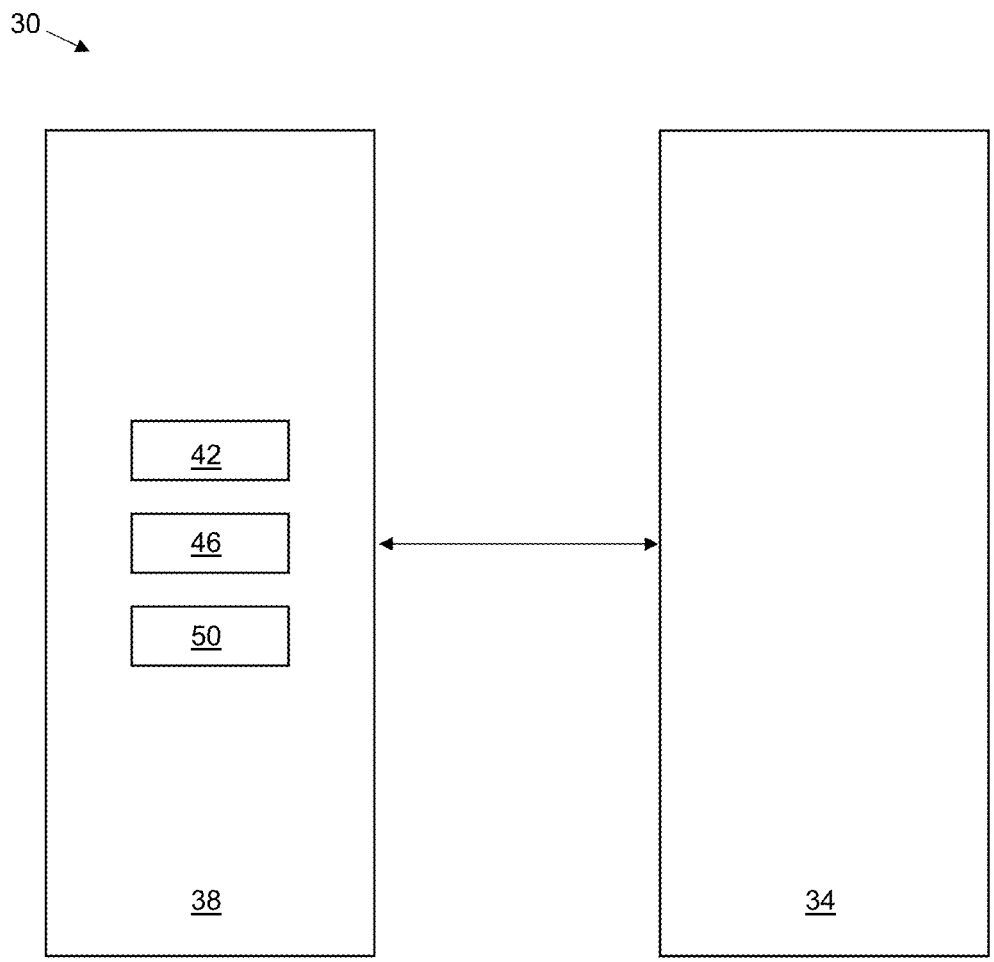
FIG. 2 is a schematic of a system that can be used to perform some of the present methods.

Referring to FIGS. 1 and 2, shown is an illustrative method 10 for analyzing one or more brain lesions of a patient and a system 30 configured to perform method 10. While some of the present methods are described with reference to system 30, system 30 is not limiting on those methods, which can be performed with any suitable system.

Some of the present methods include a step 14 of, for each of one or more—optionally, a plurality of—lesions (e.g., 58) of a patient's brain (e.g., 54), obtaining a first 3D representation (e.g., 62a) of the lesion from data taken at a first time and a second 3D representation (e.g., 62b) of the lesion obtained from data taken at a second time that is after the first time. For example, the data taken at the first time and the data taken at the second time can each be a 3D MRI image of the brain taken with an MRI device (e.g., 34) of system 30; for each of the 3D MRI images, the 3D representation of the lesion can be segmented from the image for analysis. Any suitable time can be elapsed between the first and second times; for example, the time elapsed between the first and second times can be greater than or equal to any one of, or between any two of, 3 months, 4 months, 5 months, 6 months, 1 year, 2 years, 3 years, or 4 years (e.g., between 6 months and 4 years).

To obtain the first and second 3D representations of each of the lesion(s) from the 3D MRI images, system 30 can include a processing device (e.g., 38) having one or more processors configured to receive each of those 3D images and a segmentation application (e.g., 42) by which the processor(s) can segment the 3D MRI image into one or more regions of interest (ROIs) that can each correspond to one of the brain lesion(s). An illustrative segmentation application is OsiriX from Pixmeo SARL of Geneva, Switzerland. The processing device can be a part of a computer system including standard components such as a hard drive, monitor, printer, keyboard, and mouse, and/or the like that may enable a user to interact with the processing device. To facilitate segmentation, before the MRI device images the patient's brain, a contrast agent (e.g., a paramagnetic agent such as a gadolinium-based contrast agent, an agent including a dye/pigment, and/or the like) can be administered to the patient such that the contrast agent enters the patient's bloodstream and travels to the brain. Because the blood-brain barrier at brain lesions may be compromised, a higher concentration of the contrast agent may be present at the brain lesion(s) compared to other regions in the brain. As illustrated in the MRI images in FIGS. 3A and 3B, this facilitates the identification of brain lesion(s), which can exhibit a higher intensity than other portions of the brain in the image and thus can be identified as ROIs. In other embodiments, however, the first and second 3D representations can be obtained from non-contrast MRI imaging.

Each of the first and second 3D representations of the lesion can be data that represents the geometry of the lesion (e.g., from which the volume, surface area, and/or other geometric characteristics can be calculated). For example, referring to FIGS. 4A-4D—which each depicts orthographic projections of first and second 3D representations 62a and 62b, respectively, of a lesion superimposed on one another—the first and second 3D representations can each represent the lesion as a polyhedron whose surface is defined by a plurality of polygons (e.g., triangles) (e.g., 66) and include data regarding the position of the polygons' vertices (e.g., 70) in 3D coordinates (e.g., 3D Cartesian coordinates) and/or the polygons' unit normals. As an illustration, the first and second 3D representations can each be a stereolithography (.stl) file representing the surface geometry of the lesion at the first and second times, respectively. In other embodiments, however, the first and second 3D representations can include any suitable data representing the geometry of the lesion.

Some of the present methods include a step 18 of, from the first and second 3D representations, calculating one or more lesion characteristics of each of the lesion(s). The calculated lesion characteristic(s) can include: (1) a change in the lesion's volume from the first time to the second time, (2) a change in the lesion's surface area from the first time to the second time, (3) the lesion's displacement from the first time to the second time, and/or (4) the theoretical radius ratio of the lesion at at least one of, optionally each of, the first and second times. To do so, the processing system can include a 3D imaging application (e.g., 46) by which the processor(s) can calculate the lesion characteristic(s) from the first and second 3D representations of the lesion.

To illustrate, when the first and second 3D representations each represents the lesion as a polyhedron whose surface is defined by a plurality of triangles (e.g., when each is a stereolithography file), the lesion volume can be calculated by (1) for each of the triangles, calculating the signed volume of a tetrahedron having a base defined by the triangle and a vertex at the origin and (2) summing the signed volumes to determine the total lesion volume, and the lesion surface area can be calculated by summing the areas of the triangles. The change in the lesion volume and the lesion surface area can be determined by subtracting, respectively, the volume and the surface area calculated from the first 3D representation from the volume and the surface area calculated from the second 3D representation. The change in the lesion's position can be calculated as the change in the position of the lesion's centroid from the first time to the second time (e.g., from the first and second 3D representations, respectively) and the displacement of the lesion can be calculated as the magnitude of the resulting vector.

The lesion theoretical radius ratio (R) can represent the extent to which the lesion is spherical and, for each of the first and second times, can be calculated as:

$$R = \frac{r_{SA}}{r_V} \quad (1)$$

where $r_{SA}$ is a theoretical radius of the lesion calculated from its surface area at that time based on the assumption that the lesion is spherical:

$$r_{SA} = \sqrt{\frac{SA}{4\pi}} \quad (2)$$

and $r_V$ is a theoretical radius of the lesion calculated from its volume at that time based on the assumption that the lesion is spherical:

$$r_V = \sqrt[3]{\frac{V}{\frac{4}{3}\pi}} \quad (3)$$

The closer R is to 1, the more spherical the lesion.

Some methods comprise a step 22 of characterizing whether the patient has multiple sclerosis and/or the progression of multiple sclerosis in the patient based at least in part on the calculation of the lesion characteristic(s) of each of the lesion(s). To do so, some methods include assessing whether one or more criteria are satisfied, which can be criteria whose assessment permits MS lesions to be distinguished from NSWMD lesions and/or a characterization of the progression of MS. For example, the one or more criteria can include (1) a volume-based criterion that can be satisfied when the calculated change in the lesion's volume is less than or equal to a threshold volume change, (2) an area-based criterion that can be satisfied when the calculated change in the lesion's surface area is less than or equal to a threshold surface area change, (3) a displacement-based criterion that can be satisfied when the calculated displacement of the lesion is greater than or equal to a threshold displacement, and/or (4) a deformation-based criterion that can be satisfied when the theoretical radius ratio of the lesion is greater than or equal to a threshold theoretical radius ratio at at least one of, optionally at each of, the first and second times. The processor(s) can be configured to perform the assessment of the one or more criteria and/or characterize the presence and/or progression of MS in the patient.

Satisfaction of the one or more criteria can indicate that the patient has MS and/or that MS is progressing in the patient. For example, brain lesions in patients having MS may tend to have a slower growth in volume and in surface area (and may even have a volume and a surface area that decrease with time) compared to those in patients having NSWMD, and thus a lesion having a change in volume and/or surface area that is lower than a threshold volume change and threshold surface area change, respectively, may be indicative of the presence and/or progression of MS. Brain lesions in patients having MS may also experience greater displacements compared to those in patients having NSWMD, and thus a lesion having a displacement over time that is greater than a threshold displacement may also be indicative of the presence and/or progression of MS. While the theoretical radius ratio of both MS lesions and NSWMD lesions may tend to remain substantially the same over time, NSWMD lesions may tend to be more spherical than MS lesions and, as such, a lesion having a theoretical radius ratio above a threshold radius ratio at each of the first and second times may also be indicative of the presence and/or progression of MS.

Figure 5A:
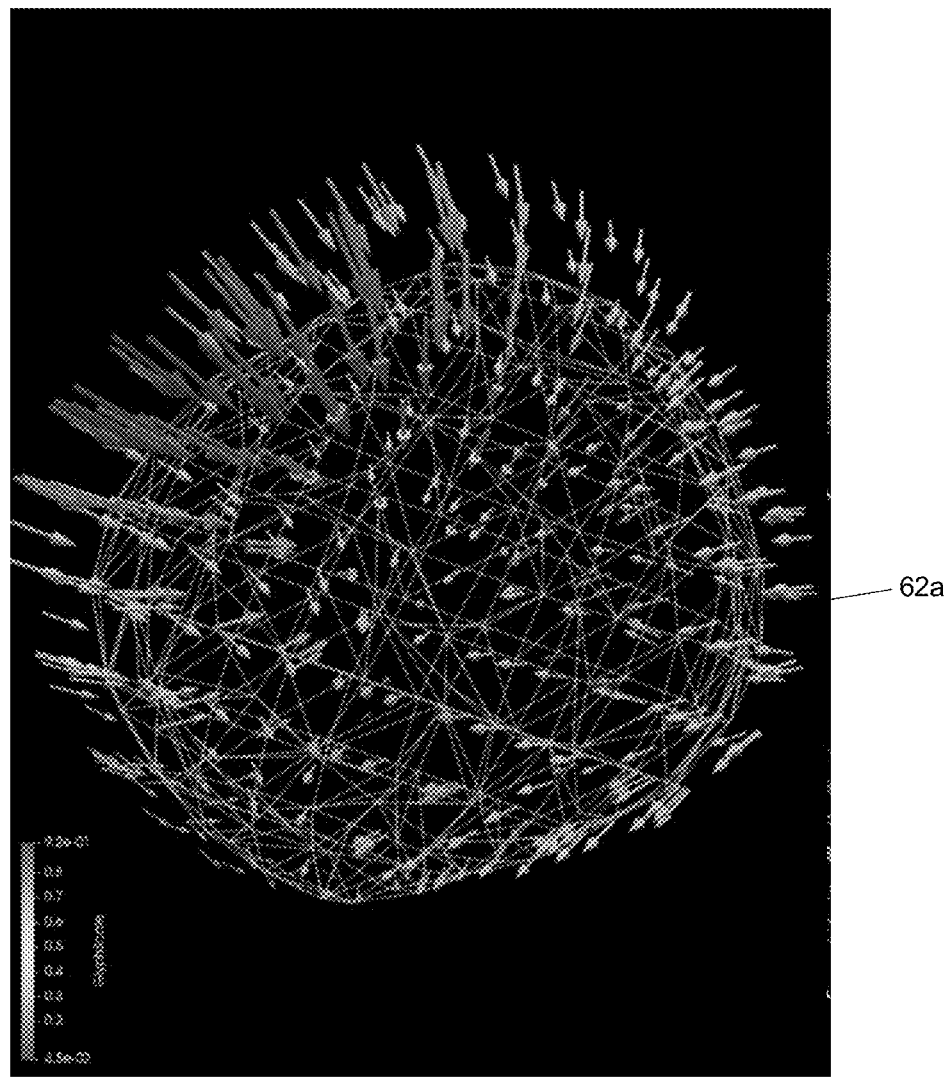
FIG. 5A shows a first 3D representation of a brain lesion of an MS patient obtained at a first time and the displacement vectors illustrating how the representation's vertices moved from the first time to a second time. The shading and size of the displacement vectors represent the magnitude of displacement; as shown, the vectors are arranged asymmetrically.
Figure 5B:
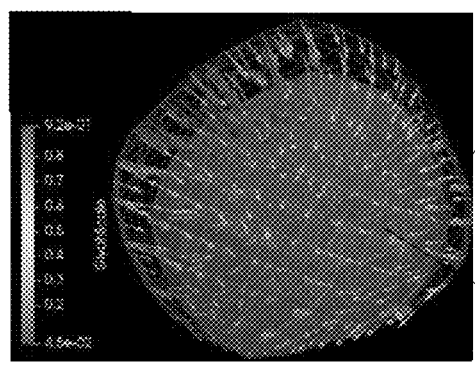
FIG. 5B shows the first 3D representation of the brain lesion of FIG. 5A (empty mesh), the displacement vectors, and a second 3D representation of the brain lesion (filled mesh) representing the lesion at the second time.
Figure 5C:
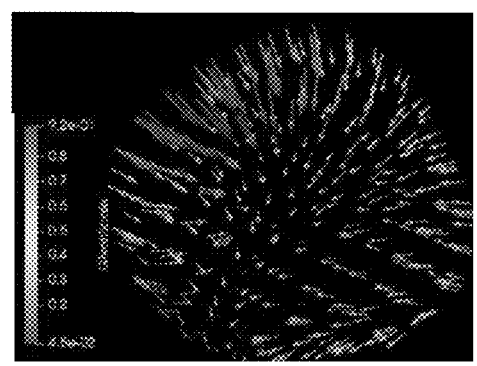
FIG. 5C illustrates the displacement vectors of FIG. 5A.
Figure 6A:
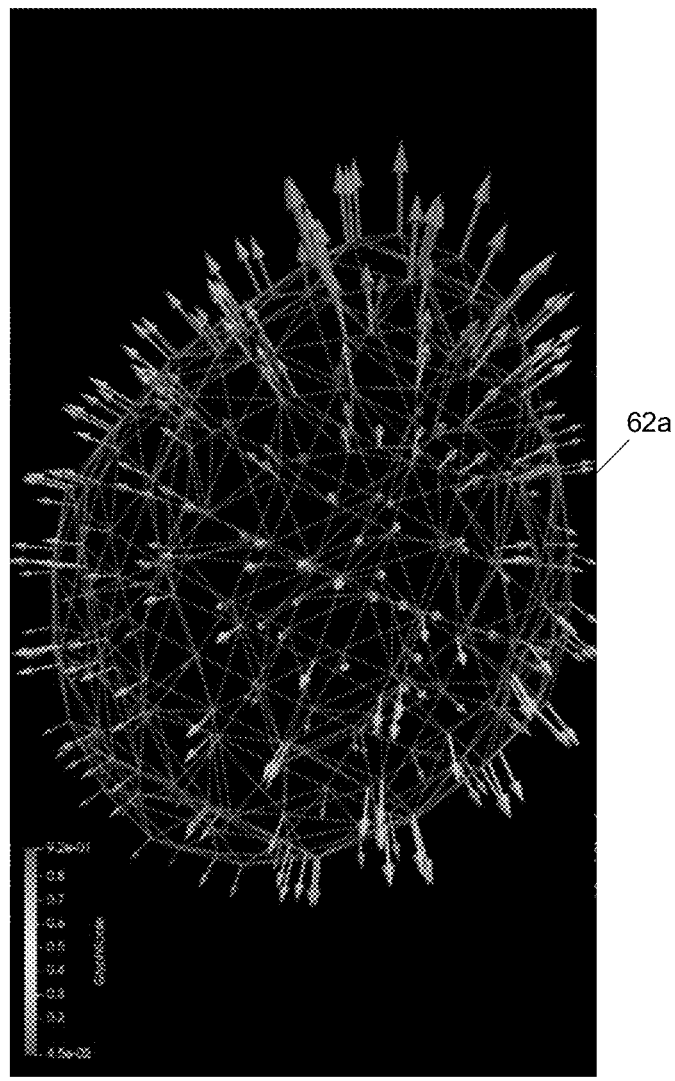
FIG. 6A shows a first 3D representation of a brain lesion of an NSWMD patient obtained at a first time and displacement vectors illustrating how the representation's vertices moved from the first time to a second time. The shading and size of the displacement vectors represent the magnitude of displacement; as shown, the vectors are arranged relatively symmetrically compared to the FIG. 5A vectors.
Figure 6B:
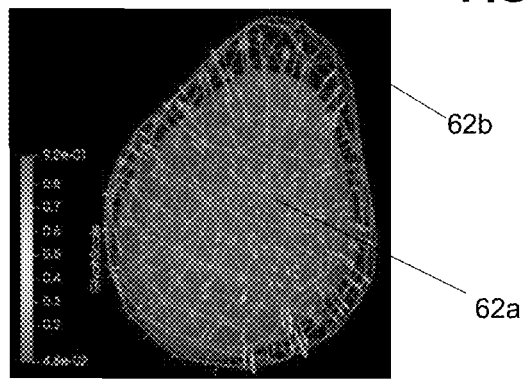
FIG. 6B shows the first 3D representation of the brain lesion of FIG. 6A (filled mesh), the displacement vectors, and a second 3D representation of the brain lesion (empty mesh) representing the lesion at the second time.
Figure 6C:
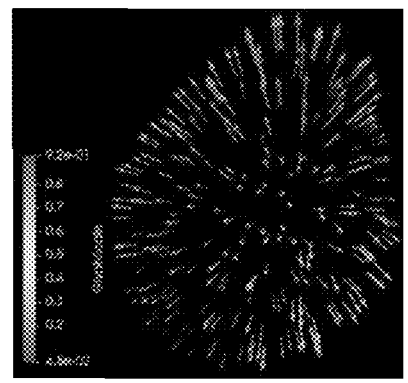
FIG. 6C illustrates the displacement vectors of FIG. 6A.

Referring to FIGS. 5A-5C and 6A-6C, for example, FIG. 5A shows a first 3D representation 62a of an MS lesion (empty mesh) with vectors illustrating the position changes of the representation's vertices from the first time to the second time, FIG. 5B shows second 3D representation 62b of the MS lesion (filled mesh) in addition to the first representation (empty mesh) and the displacement vectors of FIG. 5A, and FIG. 5C illustrates the displacement vectors of FIG. 5A alone; FIGS. 6A-6C show the same as FIGS. 5A-5C, respectively, but for an NSWMD lesion, with FIG. 6A illustrating the first 3D representation of the NSWMD lesion as an empty mesh and FIG. 6B illustrating the first and second 3D representations of the NSWMD lesion as filled and empty meshes, respectively. As shown, over time the volume and the surface area of the MS lesion decrease while the volume and the surface area of the NSWMD lesion increases. Further, the displacement vectors—when considering their magnitudes—are arranged more asymmetrically for the MS lesion compared to the NSWMD lesion, which may yield greater displacement and/or deformation.

Figure 7:
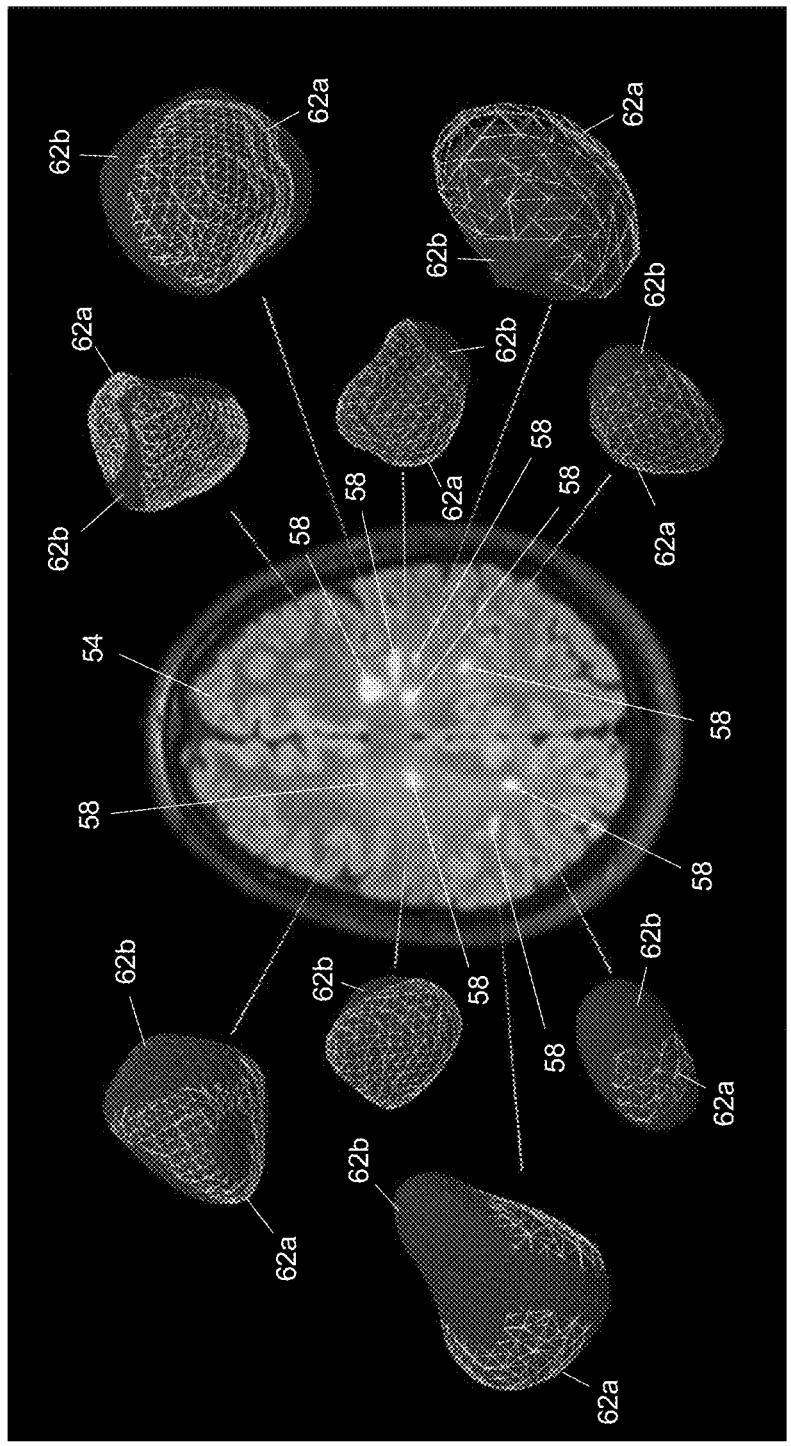
FIG. 7 shows a 2D MRI axial FLAIR image of a brain of a patient with relapsing remitting MS.

Due to the heterogeneity of MS lesions, a lesion need not satisfy all criteria to be indicative of the presence and/or progression of MS (e.g., satisfaction of at least one of the one or more criteria may at least in part support a finding that the patient has MS and/or that MS is progressing). When the brain includes multiple lesions, referencing each of those lesions to determine the geometric characteristics thereof and assess the one or more criteria based on the calculated characteristics may facilitate a more accurate characterization of the presence and/or progression of MS despite this heterogeneity. With the presence of more lesions satisfying more of the above-described criteria, it may be more likely that the patient has MS and/or that MS is progressing in the patient. For example, it can be determined that the patient has MS and/or that MS is progressing in the patient when for at least a majority of the lesions, such as greater than or equal to any one of or between any two of 50%, 60%, 70%, 80%, or 90% (e.g., at least 55%) of the lesions, at least one of the one or more criteria (e.g., the volume-based criterion, the area-based criterion, the displacement-based criterion, and/or the deformation-based criterion) is satisfied. To illustrate, and referring to FIG. 7, shown is a 2D MRI image of a brain having multiple lesions superimposed with, for each of the lesions, a first 3D representation 62*a* (empty mesh) and a second 3D representation 62*b* (filled mesh) of the lesion taken at the first and second times, respectively. While some of the lesions exhibit different geometric changes over time (e.g., with some exhibiting a reduction in volume and other exhibiting an increase in volume), the changes considered for all lesions may support an MS diagnosis.

The assessment of the one or more criteria can include determining the threshold for at least one of the criteria, optionally based at least in part on one or more patient-specific factors such as the age of the patient, the time elapsed between the first and second times, and/or the like. The processing system can include a database application (e.g., 50) comprising data regarding relevant thresholds—which may vary based on the above factors—and the processor(s) can reference that data when assessing whether the one or more criteria are satisfied. For example, for both MS lesions and NSWMD lesions, the change in volume and the change in surface area may each tend to be larger for older patients than for younger patients and, as such, the threshold volume change and/or the threshold surface area change can be determined based at least in part on the age of the patient. To illustrate, for some patients the threshold volume change can be less than or equal to any one of, or between any two of, 2.0, 1.5, 1.0, 0.5, 0.0, −0.5, −1.0, or −1.5 cubic millimeters ($mm^3$) (e.g., less than or equal to 1.5 $mm^3$ or less than or equal to 0.0 $mm^3$ (e.g., such that the lesion volume decreases)) and/or the threshold surface area change can be less than or equal to any one of, or between any two of, 2.0, 1.5, 1.0, 0.5, 0.0, −0.5, −1.0, or −1.5 square millimeters ($mm^2$) (e.g., less than or equal to 2.0 $mm^2$ or less than or equal to 0.0 $mm^2$ (e.g., such that the lesion surface area decreases)). And, for some patients, the threshold displacement can be greater than or equal to any one of, or between any two of, 0.33, 0.35, 0.37, 0.39, 0.41, 0.43, 0.45, 0.47, or 0.49 mm and/or the threshold theoretical radius ratio can be greater than or equal to any one of, or between any two of, 1.02500, 1.02501, 1.02503, 1.02504, 1.02505, 1.02506, 1.02507, 1.02508, 1.02509, 1.02600, 1.02601, 1.02602, 1.02603, or 1.02604. At least some criteria may be assessed without referencing one or more patient-specific factors (e.g., because satisfaction of those criteria may be independent of the factor(s)); as an example, the assessment of the displacement criterion and/or the deformation criterion can be performed without referencing the age of the patient (e.g., the threshold displacement and/or threshold theoretical radius ratio need not be determined based on the patient's age).

The characterization need not be based on the assessment of the lesion(s) at the first and second times alone. For example, the characterization may further be based at least in part on 3D representations of the lesion(s) obtained from data taken at other times, which similarly can be used to calculate changes in the geometries of the lesion(s) (e.g., volume changes, surface area changes, displacement, and/or the theoretical radius ratio) over time that may be indicative of the presence and/or progression of MS.

Characterizing whether the patient has MS can include a determination that the patient has MS (e.g., if at least one of the criteria is satisfied for at least one, optionally a majority, of the lesion(s)) and/or NSWMD. It can also include a determination of the patient's risk of having MS and/or NSWMD. Characterizing the progression of MS in the patient can include a determination of whether—for a patient having MS—MS is progressing or in remission. For example, some methods can be performed to assess the efficacy of a treatment; in such methods, the treatment (e.g., a medication) can be administered to the patient (e.g., between the first and second times), where a determination that MS is in remission may indicate that the treatment is effective while a determination that MS is not in remission may indicate that it is not.

The use of 3D—rather than 2D—representations of each of the lesion(s) taken at different points in time may promote the accurate diagnosis and assessment of MS and NSWMD. The time-based geometric characteristics that may vary between MS and NSWMD lesions (e.g., criteria based on the change in volume, the change in surface area, displacement, and/or theoretical radius ratio) may not be apparent in 2D representations of a lesion, even for representations obtained from high-resolution MRI images. However, these characteristics may be detectable from 3D representations of a lesion such that they can be quantified and assessed. Because MS and NSWMD lesions may exhibit different changes in at least some of these geometric characteristics over time, the assessment based on 3D representations may permit more specific and accurate diagnosis of a patient.

Figure 3A:
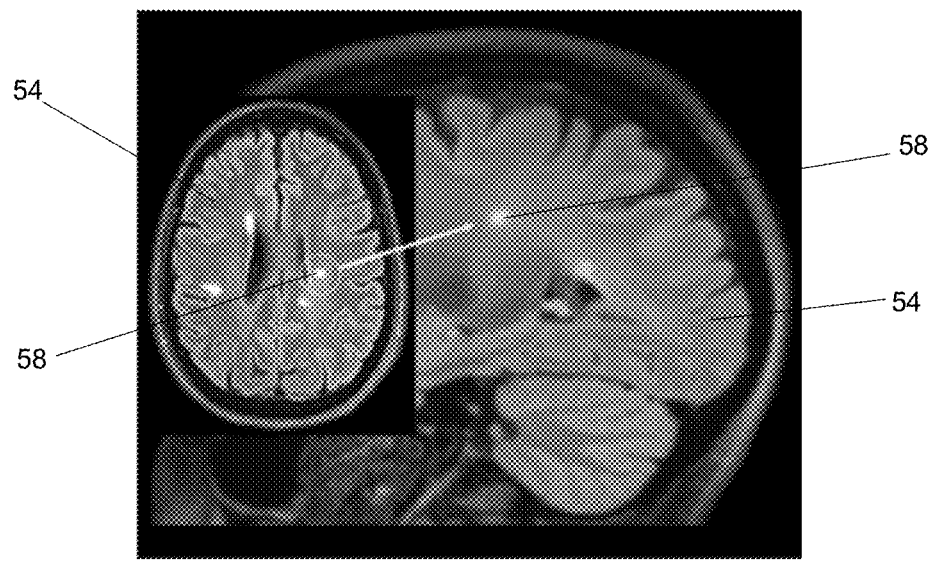
FIGS. 3A and 3B each shows a 2D MRI axial FLAIR image (left) and a 3D MRI sagittal FLAIR image (right) of a brain of a 49-year-old white woman with relapsing remitting MS that includes multiple lesions. The images of FIG. 3A were obtained at a first time and the images of FIG. 3B were obtained at a second time 1 year after the first time.
Figure 3B:
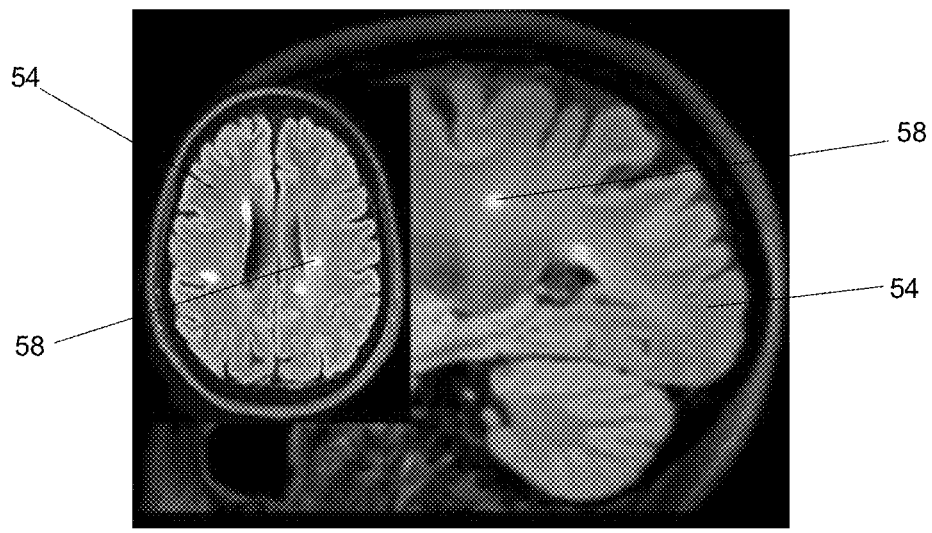
Figure 8A:
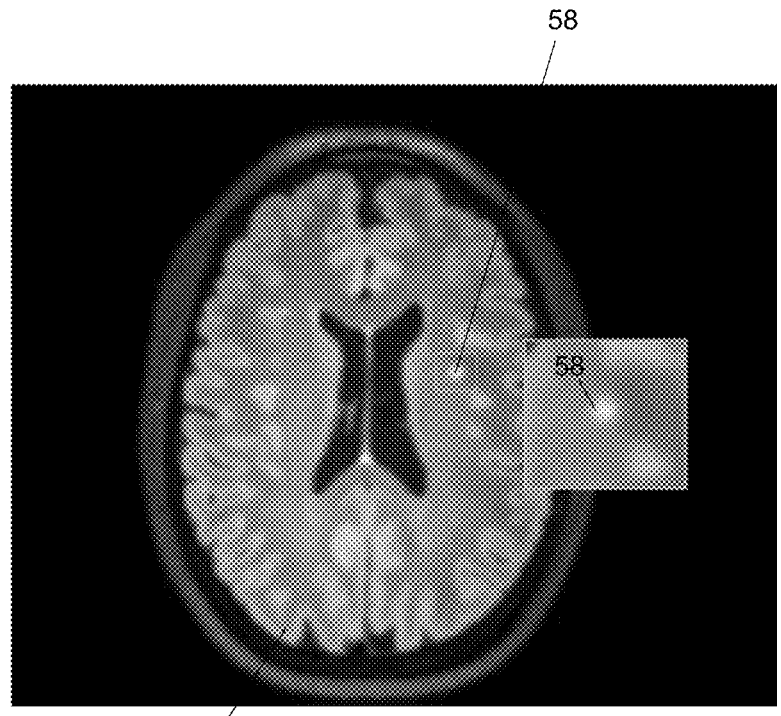
FIGS. 8A and 8B are 2D MRI axial FLAIR images of a brain of a 42-year-old white woman having NSWMD, where the FIG. 8A image was taken at a first time and the FIG. 8B image was taken at a second time that is 1 year after the first time. A single lesion is highlighted in each of the images.
Figure 8B:
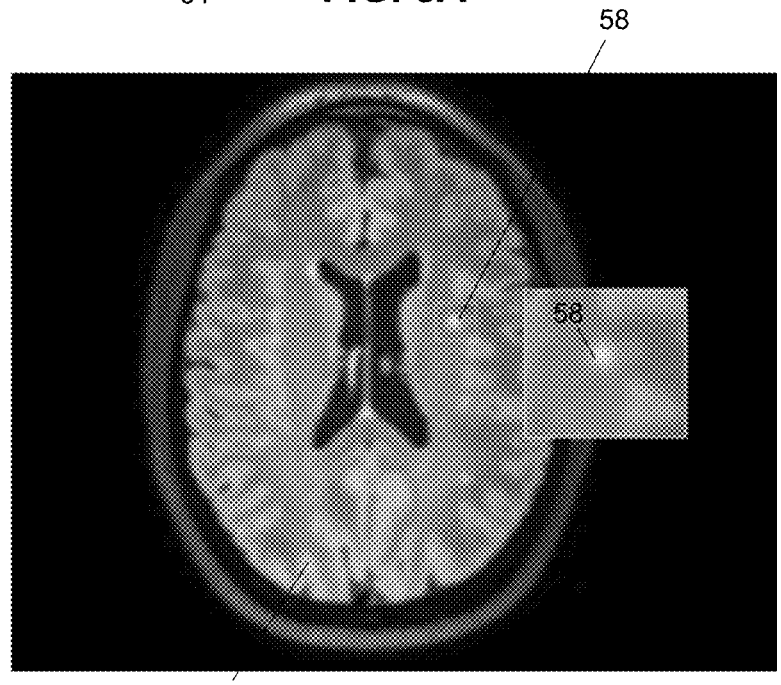

To illustrate, comparing FIGS. 3A and 3B—which each includes a 2D MRI axial FLAIR image (left) taken at first and second times, respectively, of a brain having at least one lesion 58—with FIGS. 4A-4D—which each shows first and second 3D representations 62*a* and 62*b*, respectively, of lesion 58 of FIGS. 3A and 3B—the 2D MRI images do not show a detectable change in the lesion's geometry, while the 3D representations of the lesion show the lesion experiencing a reduction in volume and in surface area and a relatively large displacement, while maintaining a non-spherical shape. The changes in the 3D representations thus indicate that the lesion may be an MS rather than an NSWMD lesion, something not detectable on the 2D MRI images. Similarly, comparing FIGS. 8A and 8B—which are also high-resolution 2D MRI axial FLAIR images taken at first and second times, respectively, of another brain having at least one lesion 58—with FIGS. 9A-9D—which each shows first and second 3D representations 62*a* and 62*b*, respectively, of lesion 58 of FIGS. 8A and 8B—the 2D MRI images again do not show a detectable change in the lesion geometry while the 3D representations show that the lesion experienced a relatively uniform growth in volume and in surface area, which may indicate that that the lesion may be an NSWMD rather than an MS lesion.

EXAMPLES

Aspects of the present invention will be described in greater detail by way of specific examples. The follow examples are offered for illustrative purposes only and are not intended to limit the invention in any manner. Those of skill in the art will readily recognize a variety of noncritical parameters that can be changed or modified to yield essentially the same results.

Example 1

Brain lesions of 34 patients were analyzed using 3D MRI. The patients were placed in two groups: (1) patients with a confirmed MS diagnosis based on established criteria and results from supporting para-clinical studies (i.e., cerebrospinal fluid profiles, electrophysiological data, and/or serological results) to the exclusion of other disease states, and (2) patients with a history of brain anomalies atypical for in situ demyelination based on the observed radiological phenotype and formal imaging interpretations performed by a board-certified neuroradiological and clinical impressions from an MS specialist.

Imaging was performed with a 3T MRI scanner from Philips Medical Systems, Cleveland Ohio, using a 32-channel phased array coil for reception and body coil for transmission. Each MRI study included scout localizers, 3D high-resolution inversion recovery spoiled gradient-echo T1-weighted isotropic (1.0×1.0×1.0 mm³, TE/TR/TI=3.7/8.1/864 ms, flip angle 12 degrees, 256×220×170 mm³ FOV, number of excitations (NEX)=1,170 slices, duration: 4:11 min), 3D fluid-attenuated inversion recovery (FLAIR) (1.1× 1.1×1.1 mm³, TE/TR/TI=350/4800/1600 ms, flip angle 90 degrees, 250×250×180 mm³ FOV, NEX=1,163 slices, duration: 5:02 min), and 3D T2 sequence acquired in sagittal plane (1.0×1.0×1.0 mm³, TE/TR/TI=229/2500/1600 ms, flip angle 90 degrees, 250×250×180 mm³ FOV, NEX=1,164 slices, duration: 4:33 min). For each patient, MRI was performed at two points in time.

Lesions were segmented from the MRI images without knowledge of the patients' clinical histories, current or past treatments, or disease durations. The selection of focal brain lesions with an area greater than 3 mm² within the supratentorial region were verified from simultaneously viewed 3D high-resolution FLAIR and T2-weighted sequences. The segmented lesions were saved as region of interest files for analysis. The mesh analysis software used for visualization of the lesions was ParaView from National Technology & Engineering Solutions of Sandia, LLC (NTESS) of Albuquerque, N. Mex. and Kitware Inc. of Clifton Park, N.Y. Over all 34 patients assessed, 405 lesions were segmented for analysis: 248 from the MS group and 157 from the NSWMD group. The change in volume, change in surface area, and displacement from the first time to the second time of each of the lesions were calculated. For each of the lesions, the theoretical radius ratio of the lesion at the first time ($R_1$) and at the second time ($R_2$) were also calculated. TABLE 1 sets forth the clinical data (e.g., patient characteristics) and lesion data (e.g., lesion characteristics calculated during the study) below. $P_{25}$ and $P_{75}$ are the 25$^{th}$ and 75$^{th}$ percentiles, respectively.

TABLE 1

Clinical and Lesion Data for 3D MRI Longitudinal Study

| | Multiple Sclerosis Group | Non-Specific White Matter Disease Group |
|---|---|---|
| Clinical Data | | |
| Patients | 23 | 11 |
| Mean Age (std. dev.) | 42.2 years (11.9) | 52.5 years (7.63) |
| Female (% of patients) | 14 (60.9%) | 11 (100%) |
| Race (% of patients) | | |
| White | 21 (91.3%) | 10 (90.9%) |
| African American | 2 (8.7%) | 0 (0%) |
| Asian | 0 (0%) | 1 (9.1%) |
| Hispanic (% of patients) | 2 (8.7%) | 2 (18.2%) |
| Median Disease Duration ($P_{25}$, $P_{75}$) | 1.99 years (0.54, 5.94) | — |
| Median Number Lesions ($P_{25}$, $P_{75}$) | 11 (6.5, 14.5) | 14 (12, 17) |
| Lesion-Level Data | | |
| Lesions Analyzed | 248 | 157 |
| Median Duration Between MRI Imaging ($P_{25}$, $P_{75}$) | 1.65 years (1.26, 1.91) | 2.74 years (1.72, 3.46) |
| Median Change in Volume Between MRI Timepoints ($P_{25}$, $P_{75}$) | −2.32 mm³ (−9.67, 3.48) | 3.94 mm³ (−0.65, 10.1) |
| Median Change in Surface Area Between MRI Timepoints ($P_{25}$, $P_{75}$) | −2.16 mm² (−8.19, 3.51) | 4.18 mm² (−0.63, 8.93) |
| Median (($R_1$ − 1) × 100) ($P_{25}$, $P_{75}$) | 3.38 (2.41, 4.63) | 2.17 (1.54, 2.81) |
| Median (($R_{ij2}$ − 1) × 100) ($P_{25}$, $P_{75}$) | 3.46 (2.48, 4.60) | 2.10 (1.52, 3.06) |
| Median Displacement ($P_{25}$, $P_{75}$) | 0.39 mm (0.28, 0.56) | 0.32 mm (0.22, 0.42)† |

†Based on n = 140.

To determine the differences between MS lesions and NSWMD lesions, a statistical analysis was performed using RStan in R to control for differences such as patient age and time between MRI studies. For changes in volume and in surface area, Bayesian linear mixed effects regression models were constructed to fit the differences between the MS lesions' changes in volume and in surface area and the NSWMD lesions' changes in volume and in surface area. Random effects of the model included subject-specific random intercepts to account for intra-subject correlation; the random intercepts were assumed to be randomly sampled from a Student's t distribution because there was evidence of greater kurtosis than that allowed by a normal distributions. The residuals were also assumed to be randomly sampled from a Student's t distribution with diagnosis-specific degrees-of-freedom parameters defined for both groups because there was evidence of differing kurtosis and variability.

For displacement, the difference between the MS lesions' median displacement and the NSWMD lesions' median displacement was also analyzed with a Bayesian linear mixed effects regression model that was fit to the log-transformed magnitude differences. Random effects of the model included subject-specific random intercepts to account for intra-subject correlation between lesions; the random intercepts were assumed to be randomly sampled from a normal distribution. The residuals were assumed to be randomly sampled from a Student's t distribution and diagnosis-specific degrees-of-freedom parameters defined for both groups.

For theoretical radius ratio, a Bayesian linear mixed effects regression model was also used to assess the difference in theoretical radius ratios between the MS lesions and the NSWMD lesions while controlling for patient age, time elapsed between MRI studies, the interaction between patient age and time elapsed, and the interaction between diagnosis and time elapsed. Random effects of the model included subject-specific random intercepts to account for intra-subject correlation and lesion-specific random intercepts to account for intra-lesion correlation. The subject-specific random intercepts were assumed to be randomly sampled from a normal distribution.

Figure 10A:
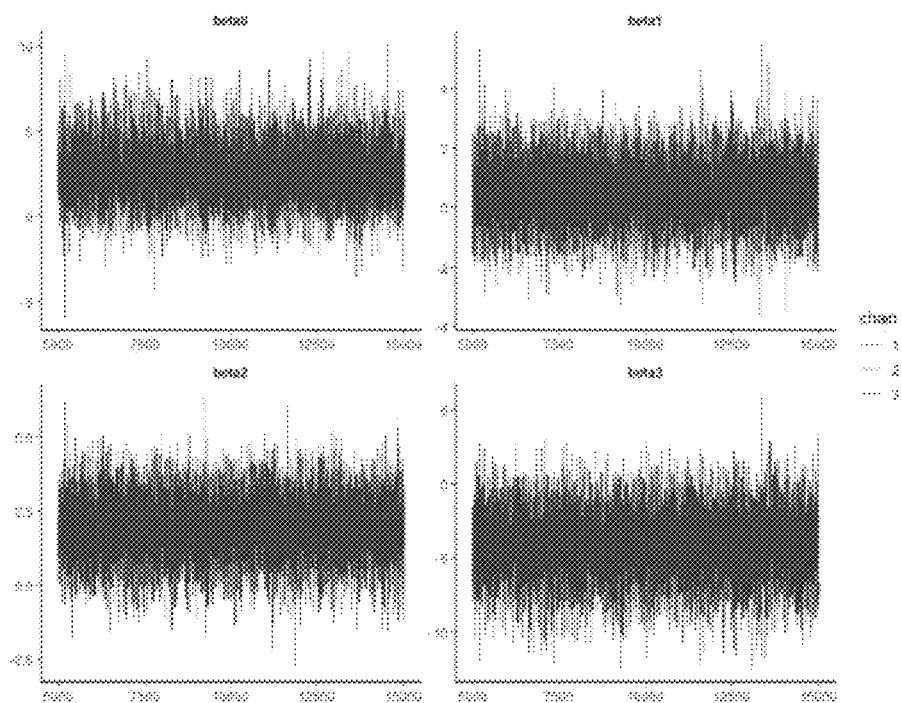
FIGS. 10A and 10B are trace plots for the statistical analysis of lesion volume performed in Example 1.
Figure 10B:
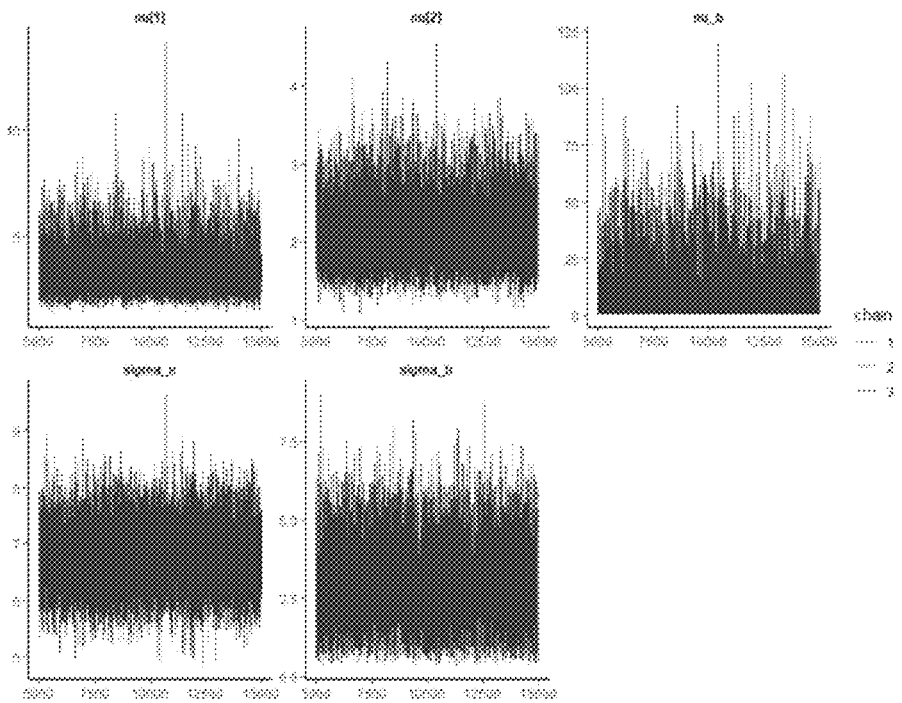
Figure 10C:
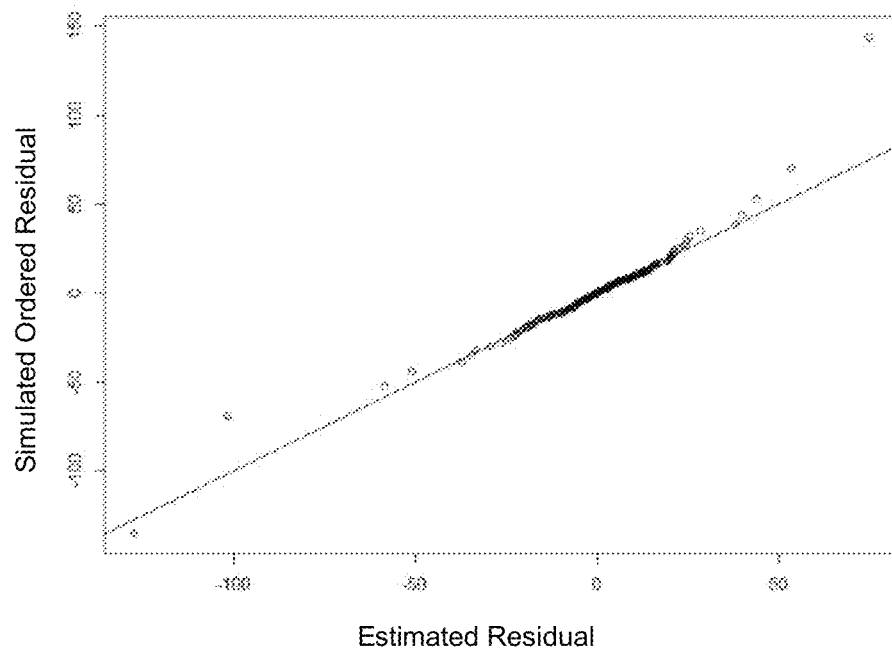
FIGS. 10C-10E are plots used as posterior predictive checks of the distribution of response, random effect distribution, and residual versus fitted values, respectively, for the statistical analysis of lesion volume performed in Example 1.
Figure 10D:
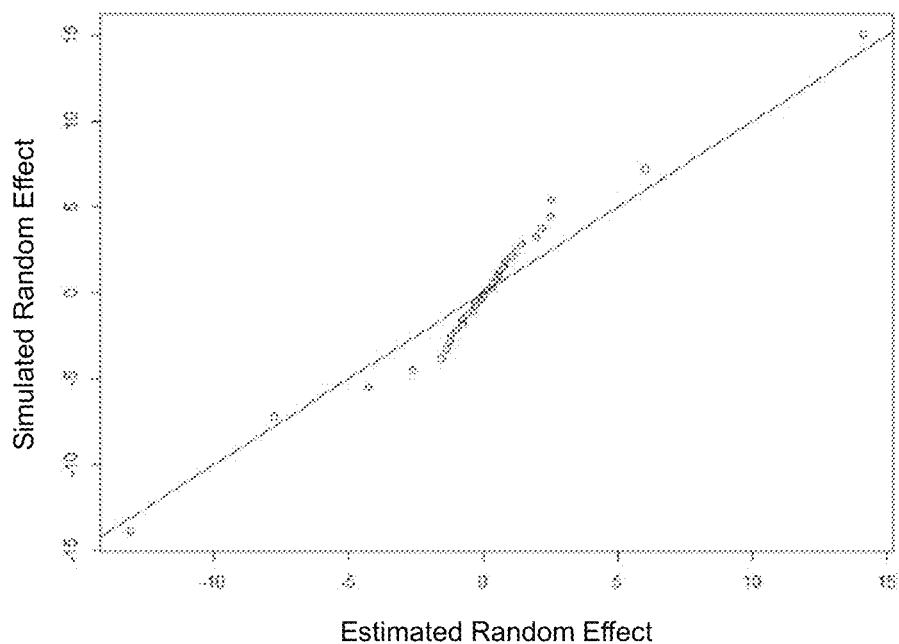
Figure 10E:
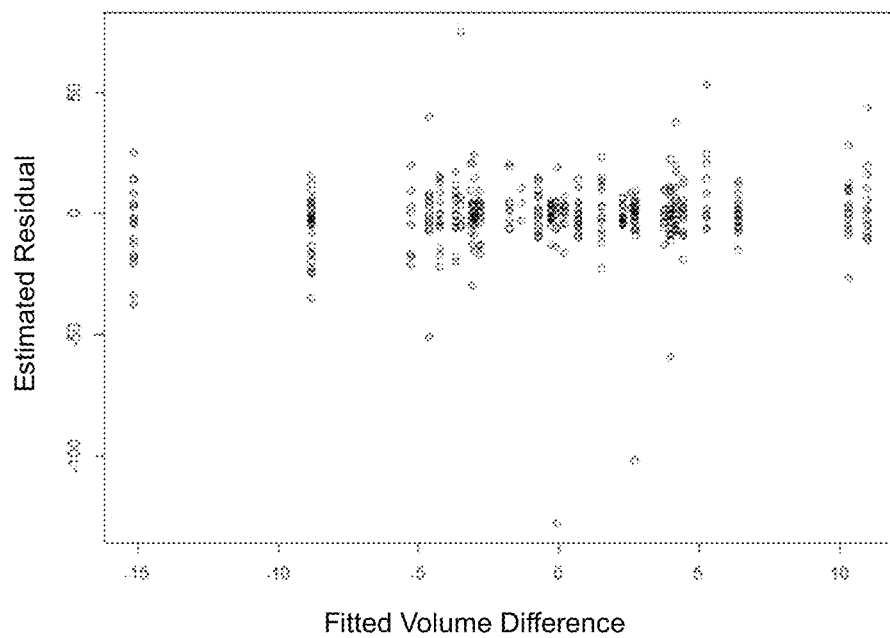
Figure 10F:
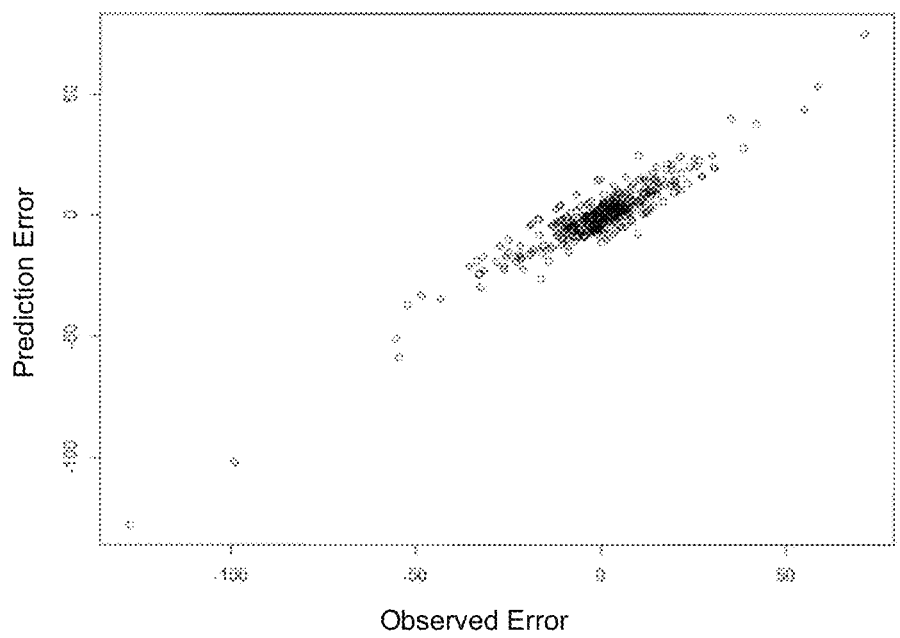
FIG. 10F is a plot showing posterior predictive error versus the observed values for the statistical analysis of lesion volume performed in Example 1.
Figure 11A:
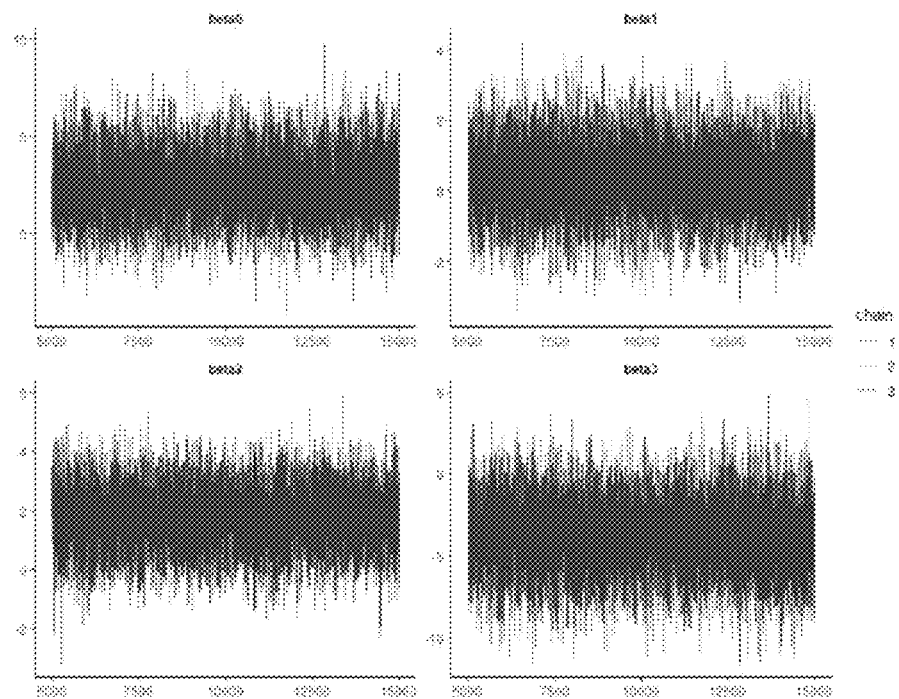
FIGS. 11A and 11B are trace plots for the statistical analysis of lesion surface area performed in Example 1.
Figure 11B:
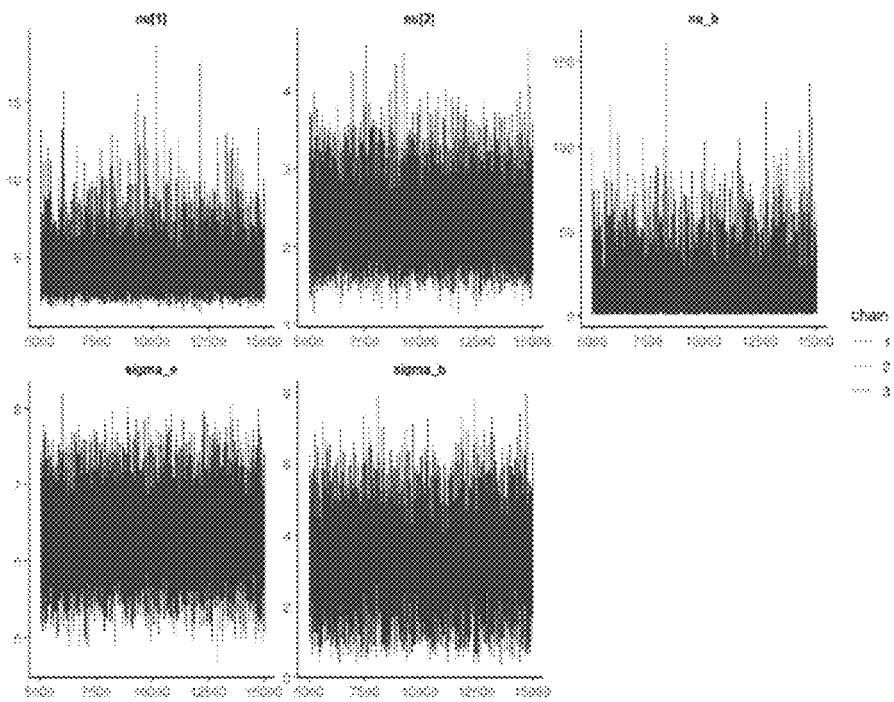
Figure 11C:
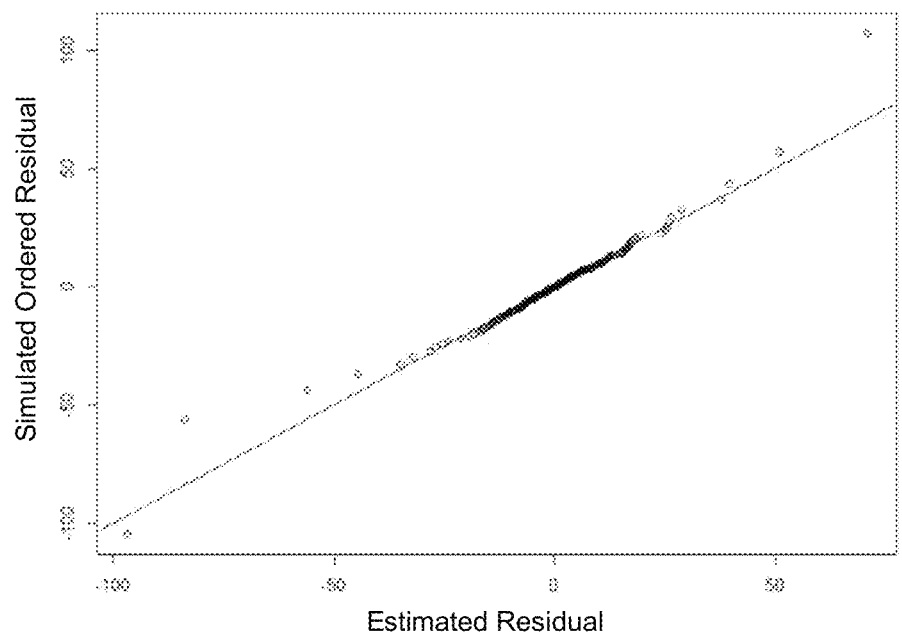
FIGS. 11C-11E are plots used as posterior predictive checks of the distribution of response, random effect distribution, and residual versus fitted values, respectively, for the statistical analysis of lesion surface area performed in Example 1.
Figure 11D:
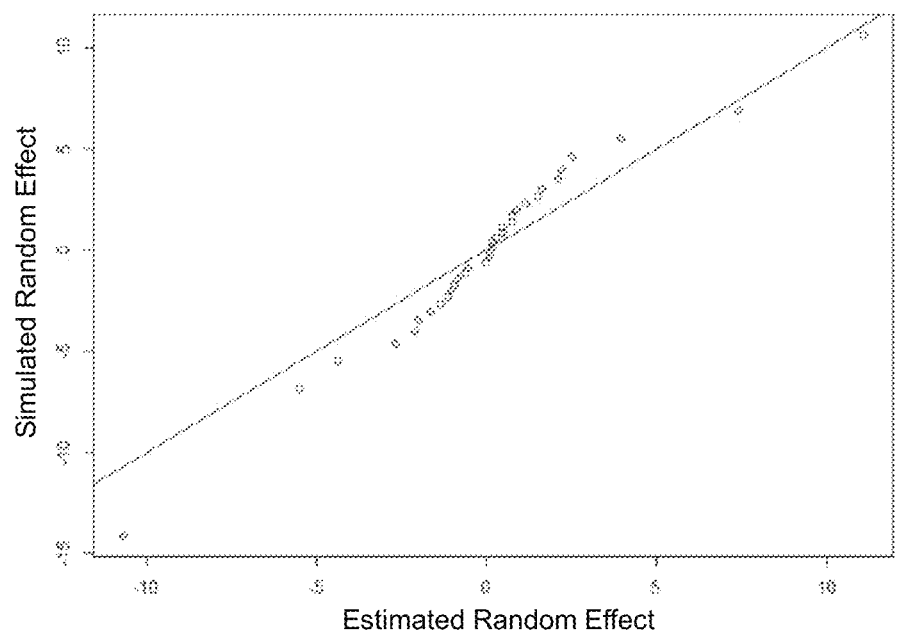
Figure 11E:
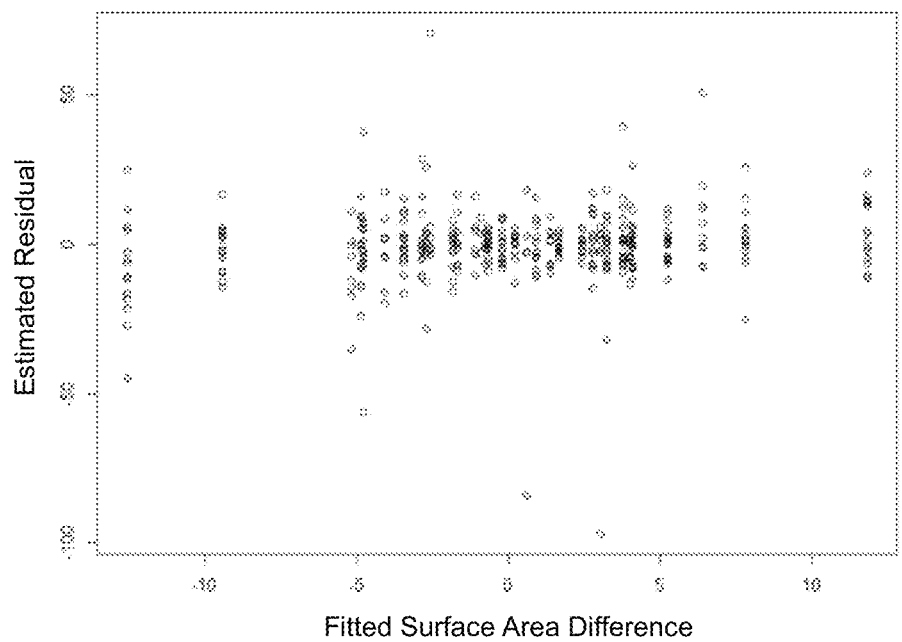
Figure 11F:
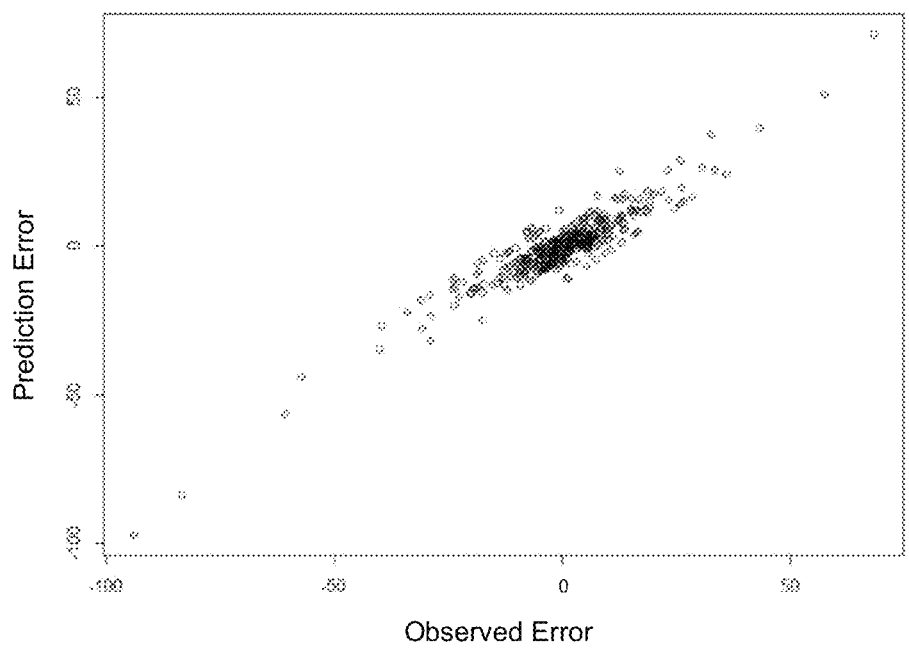
FIG. 11F is a plot showing posterior predictive error versus the observed values for the statistical analysis of lesion surface area performed in Example 1.
Figure 12A:
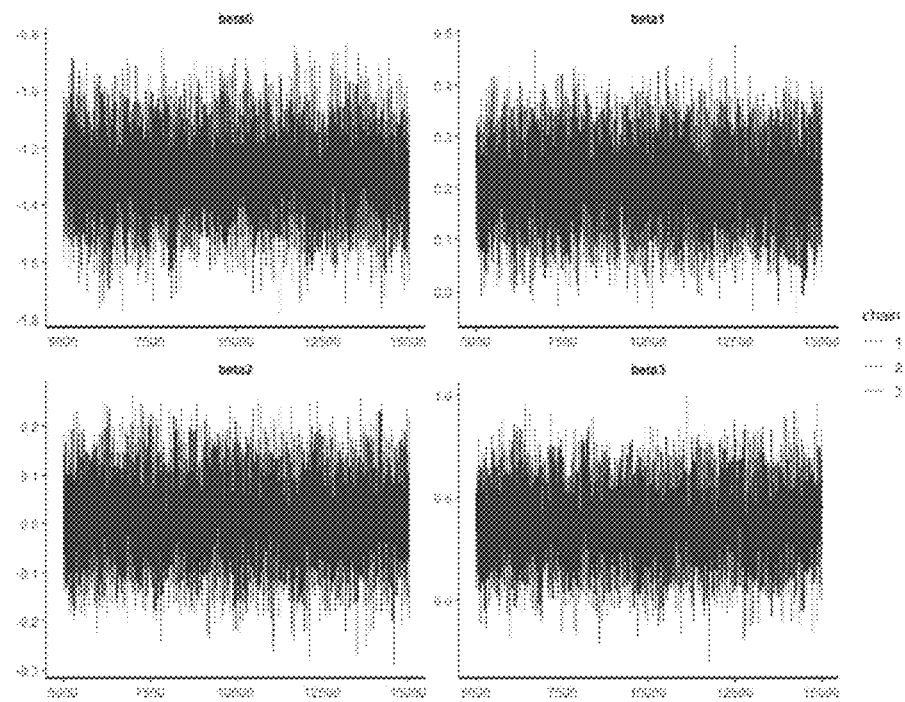
FIGS. 12A and 12B are trace plots for the statistical analysis of lesion displacement performed in Example 1.
Figure 12B:
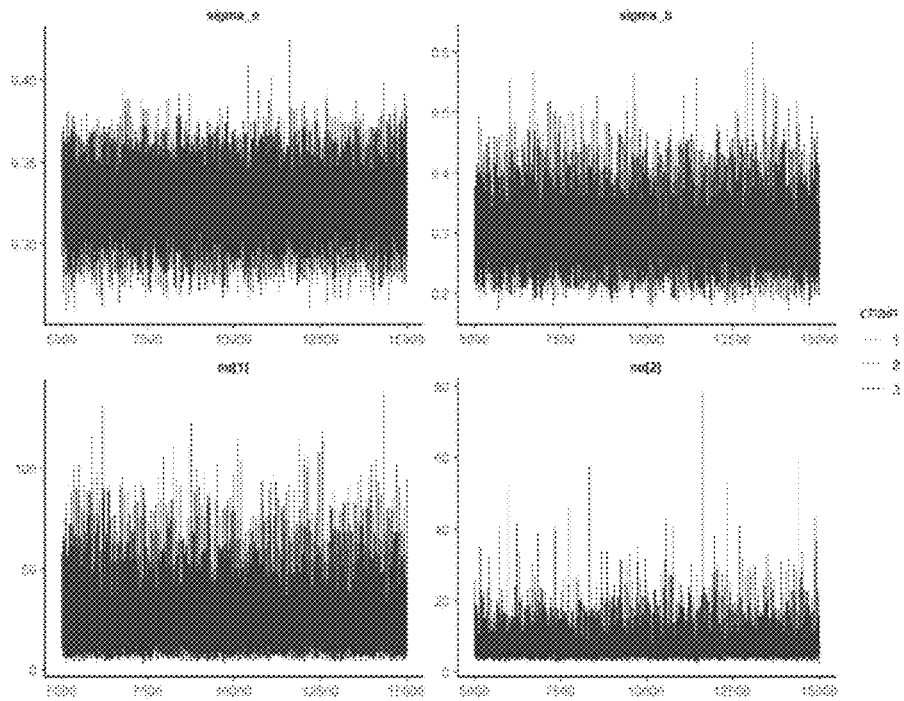
Figure 12C:
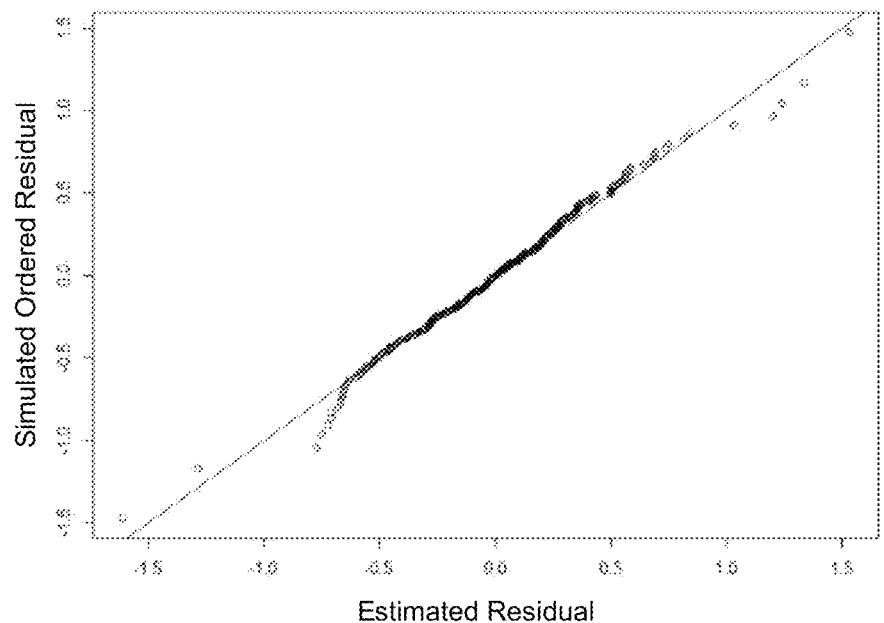
FIGS. 12C-12E are plots used as posterior predictive checks of the distribution of response, random effect distribution, and residual versus fitted values, respectively, for the statistical analysis of lesion displacement performed in Example 1.
Figure 12D:
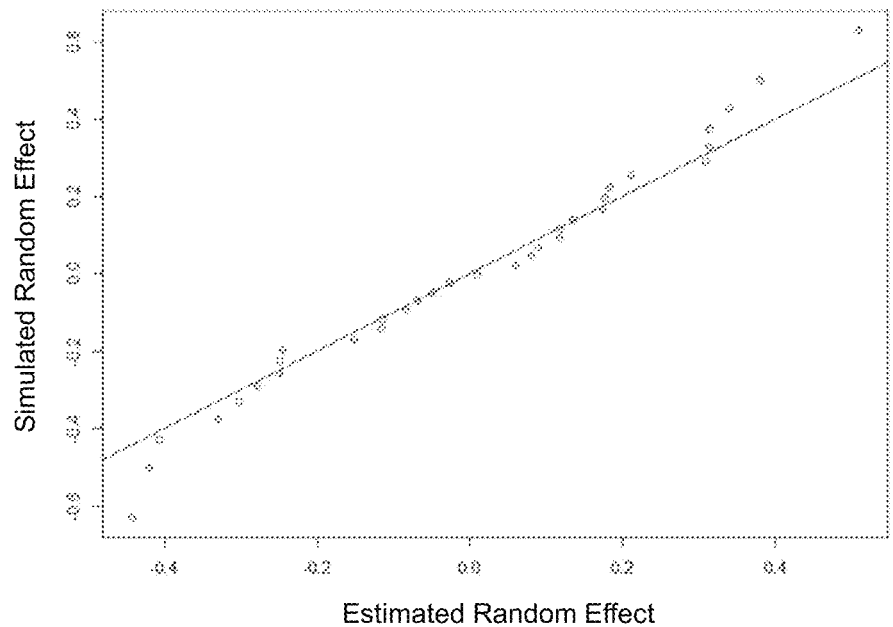
Figure 12E:
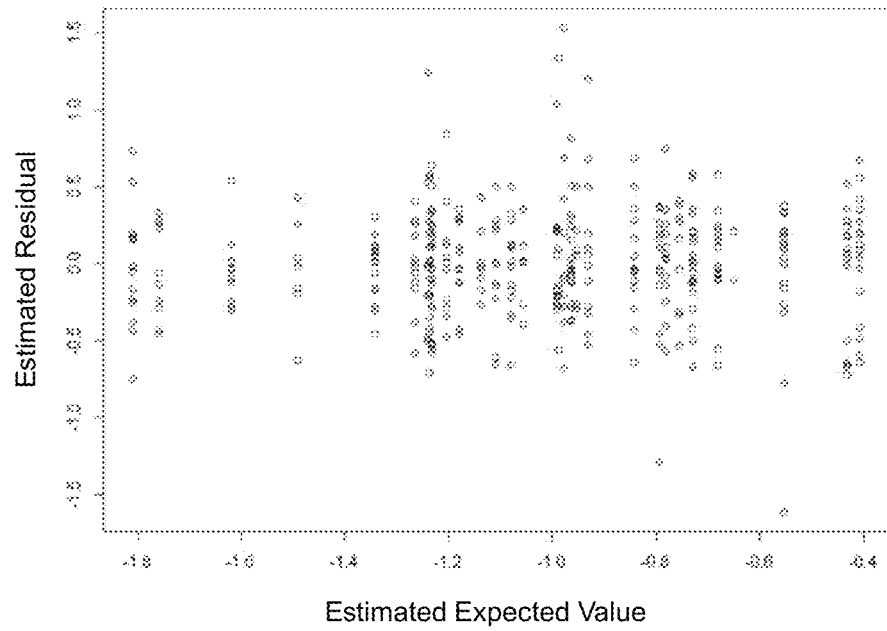
Figure 12F:
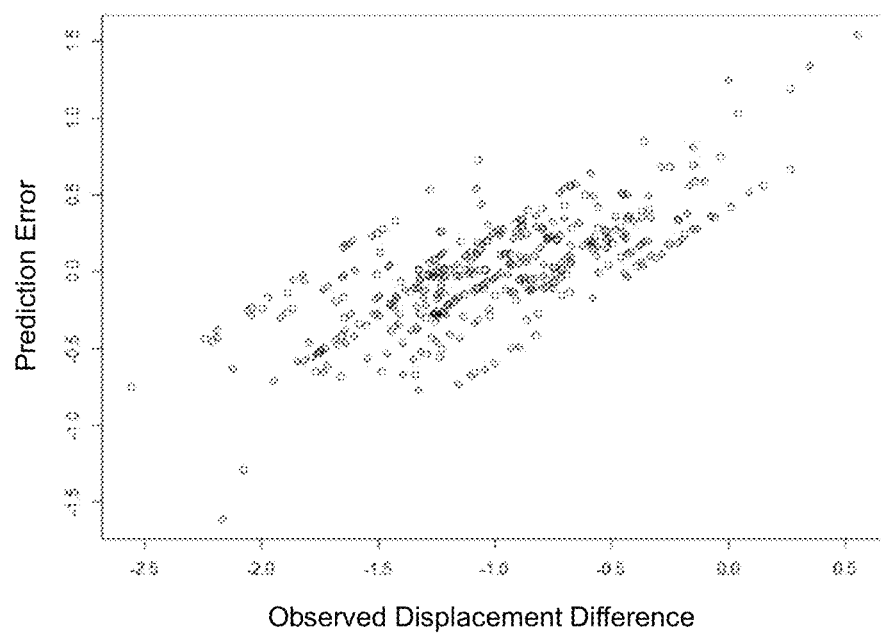
FIG. 12F is a plot showing posterior predictive error versus the observed values for the statistical analysis of displacement performed in Example 1.
Figure 13A:
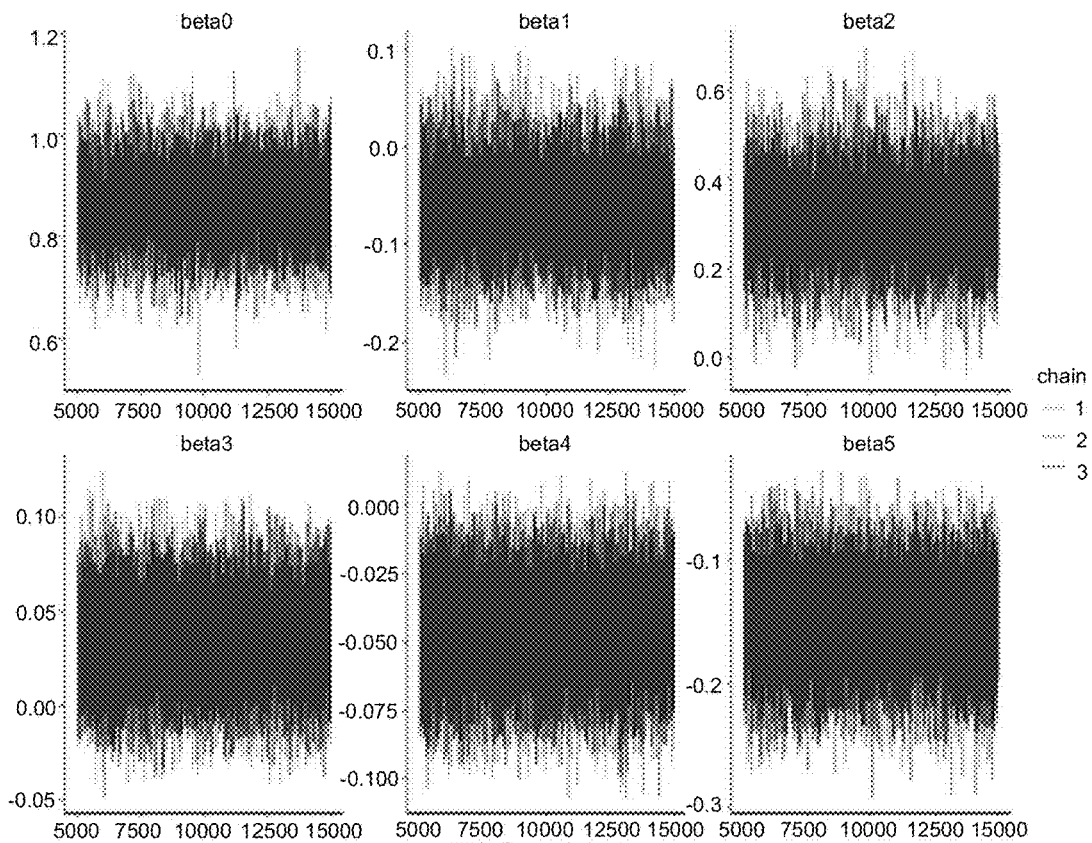
FIGS. 13A-13C are trace plots for the statistical analysis of lesion theoretical radius ratio performed in Example 1.
Figure 13B:
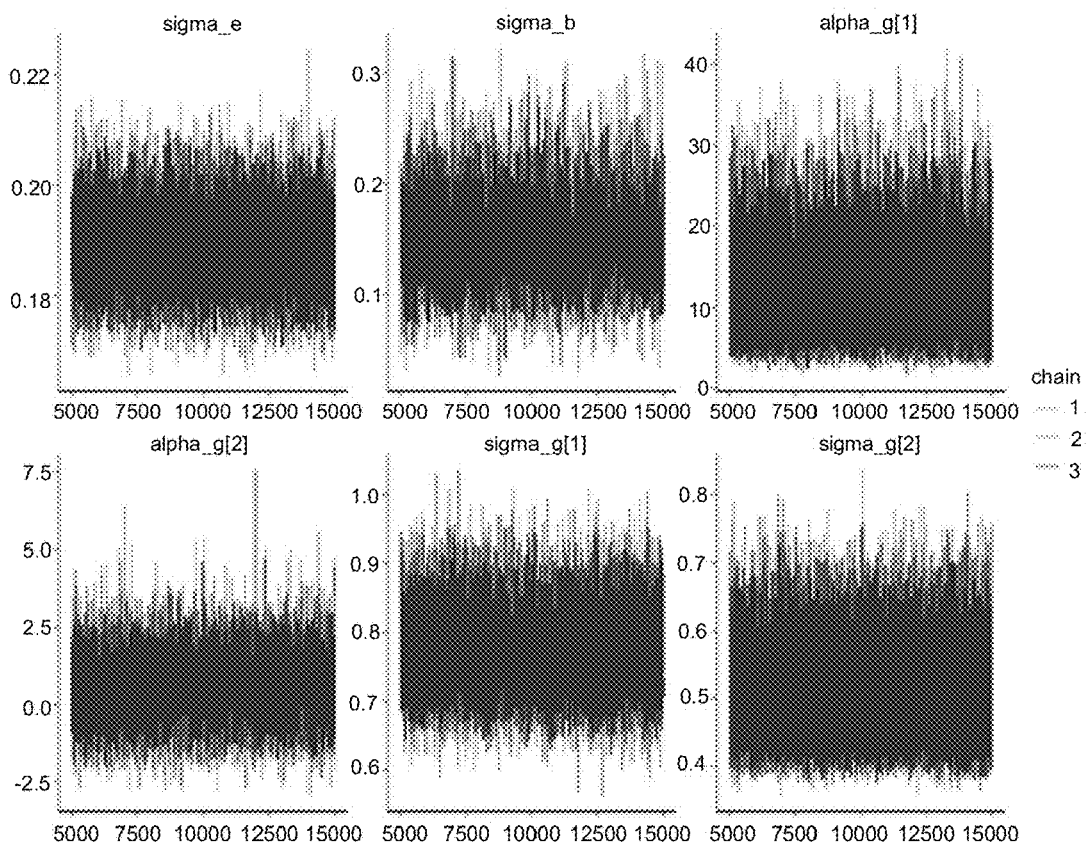
Figure 13C:
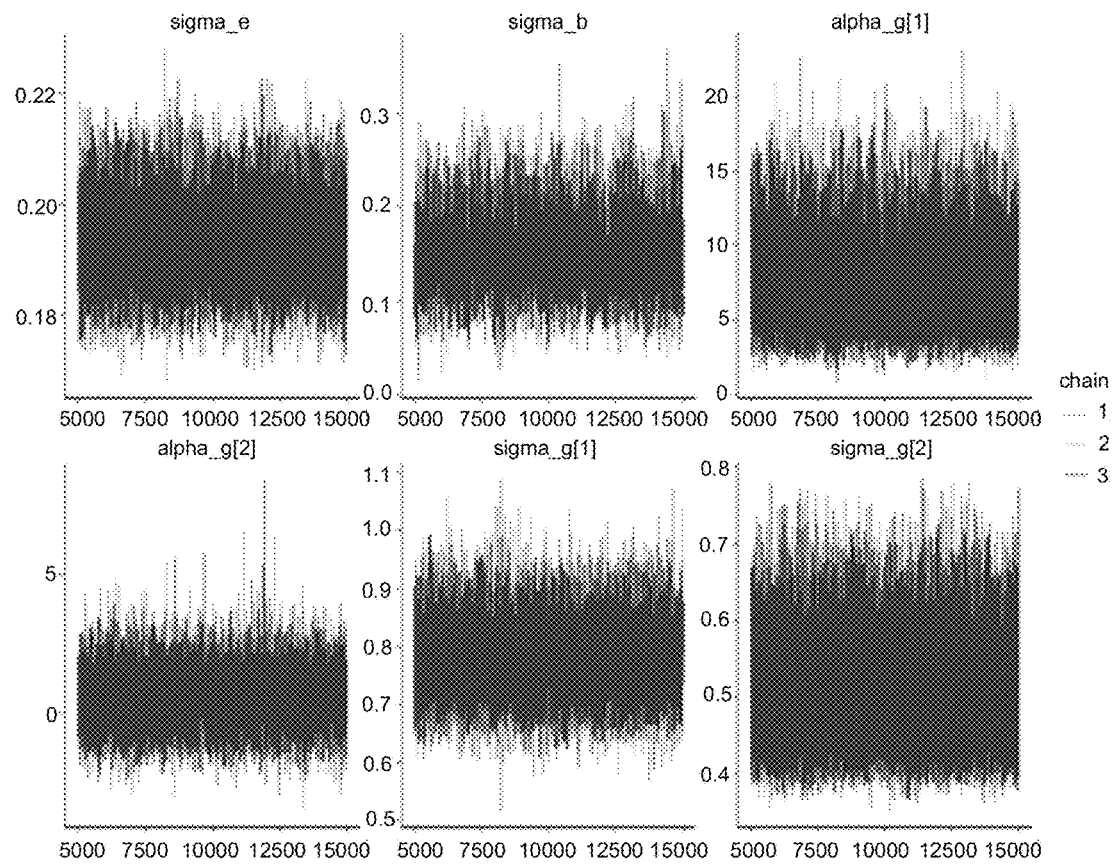
Figure 13D:
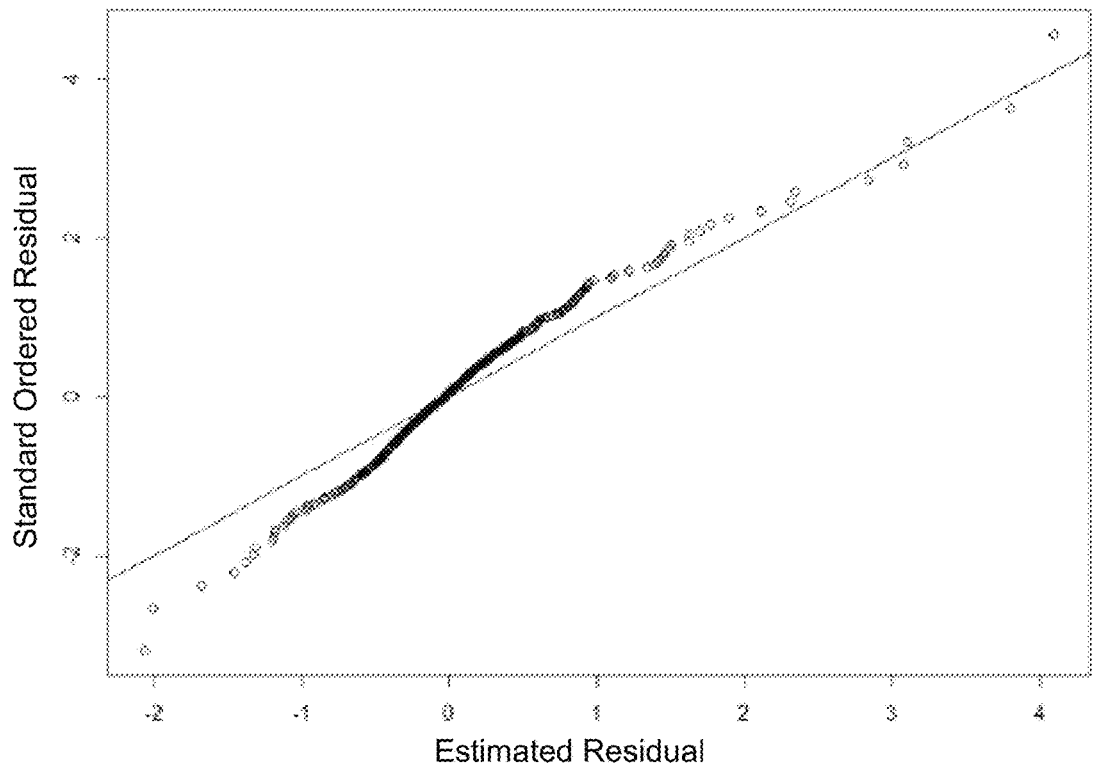
FIGS. 13D-13G are plots used as a posterior predictive checks of the distribution of response, patient-level random effect distribution, lesion-level random effect distribution, and residual versus fitted values, respectively, for the statistical analysis of lesion theoretical radius ratio performed in Example 1.
Figure 13E:
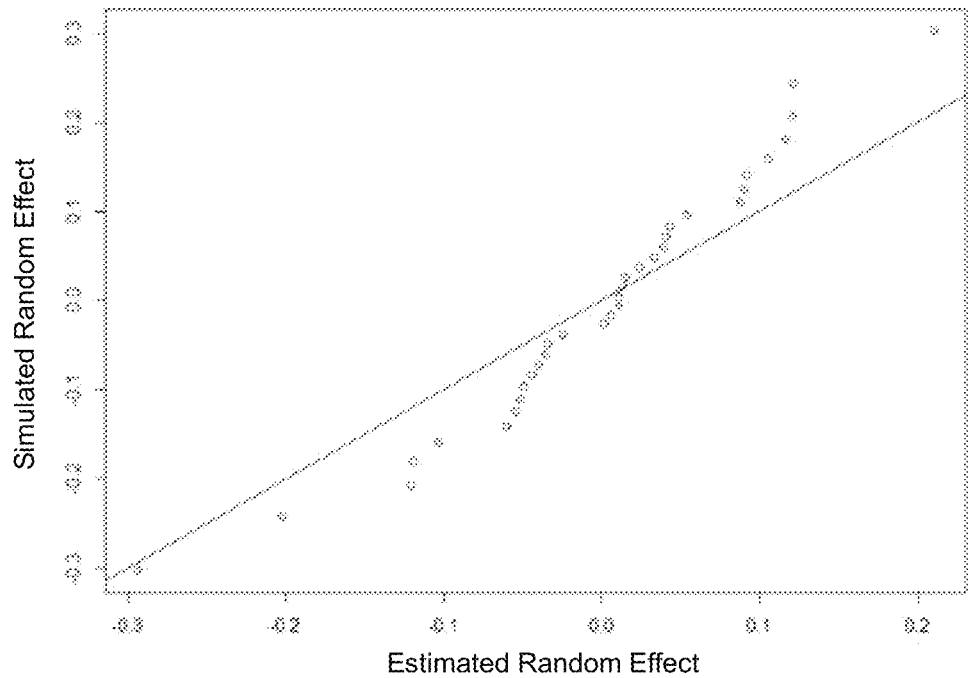
Figure 13F:
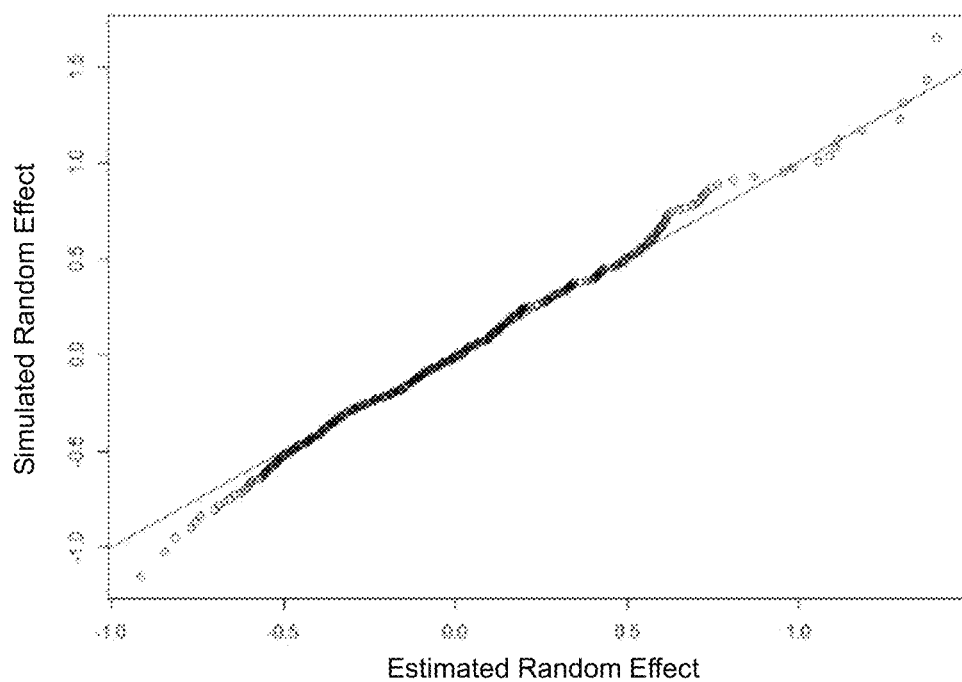
Figure 13G:
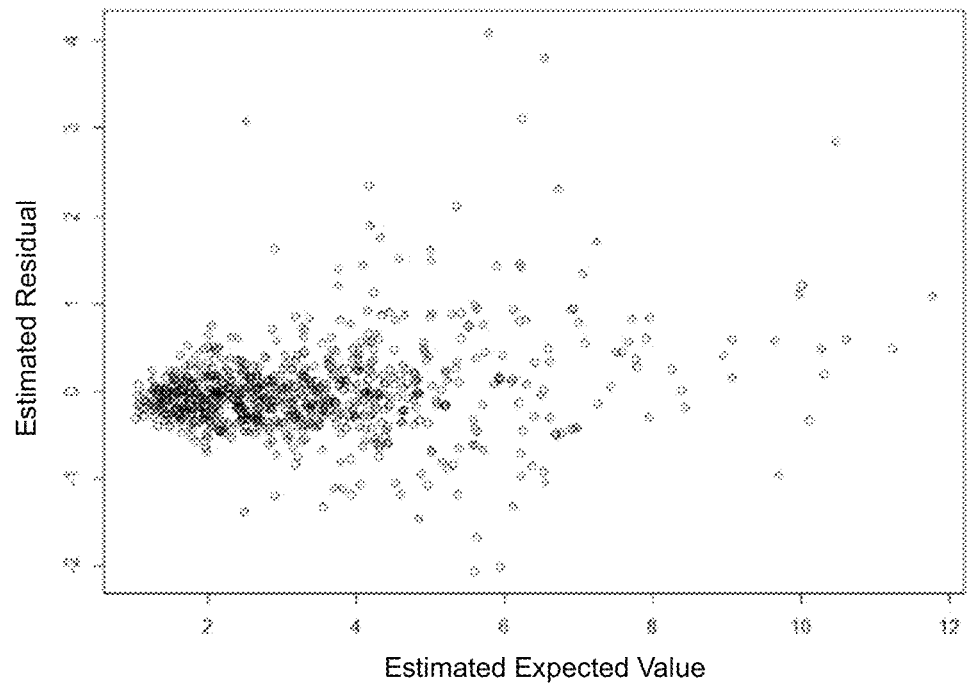
Figure 13H:
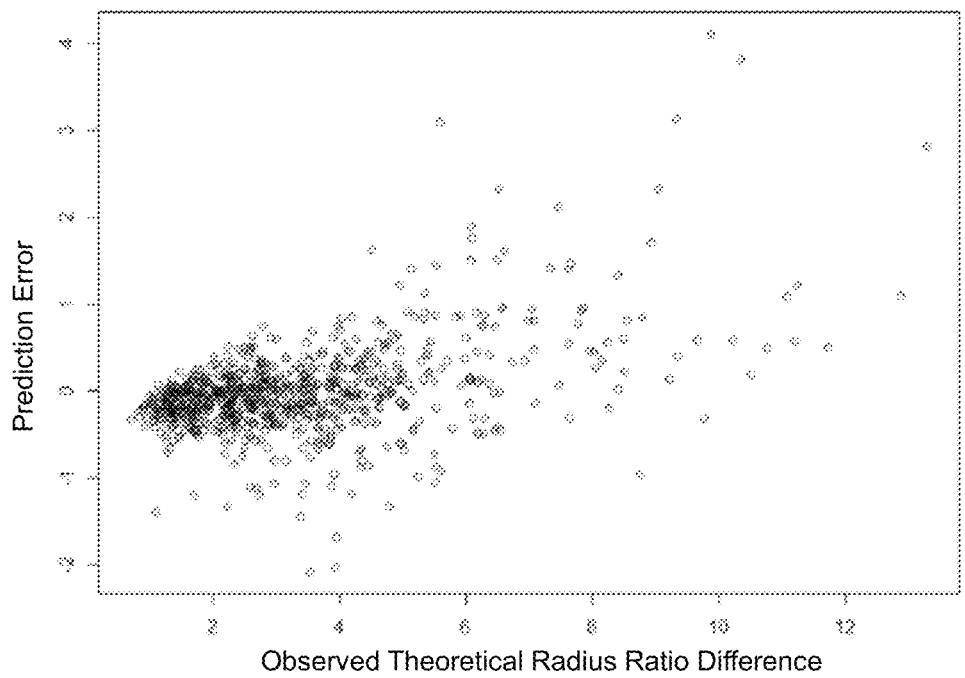
FIG. 13H is a plot showing posterior predictive error versus the observed values for the statistical analysis of lesion theoretical radius ratio performed in Example 1.

For all of the Bayesian models used, the coefficients were given N(0, 100) prior distributions. Degrees-of-freedom for all Student's t distributions were given a Gamma (2, 0.1) prior distribution, all standard deviation (or scale) parameters were given a Half-Cauchy (0, 2.5) prior distribution, and the shape parameters for all Skew-Normal distributions were given a N(0, 100) prior distribution. To ensure model convergence, three chains using 15,000 iterations with a 5,000 iteration burn-in were run and convergence was examined using the trace plots of model parameters (FIGS. 10A-10B for lesion volume, FIGS. 11A-11B for lesion surface area, FIGS. 12A-12B for lesion displacement, and FIGS. 13A-13C for lesion theoretical radius ratio). When convergence was verified, the model was run with a single chain having 15,000 iterations with a 5,000 iteration burn-in. To assess the distributional assumptions for the response, the sorted posterior mean of the residuals was plotted against the mean of the ordered posterior predictive residuals (FIG. 10C for lesion volume, FIG. 11C for lesion surface area, FIG. 12C for lesion displacement, and FIG. 13D for lesion theoretical radius ratio). A plot of the posterior mean of the random effects versus the mean of the posterior predictive random effects was also created (FIG. 10D for lesion volume, FIG. 11D for lesion surface area, FIG. 12D for lesion displacement, and FIGS. 13E and 13F for theoretical radius ratio). A plot of the posterior mean of the residuals versus the posterior mean of the fitted values was generated to examine the homogeneity of variance assumptions for models assuming normal or Student's t distributed errors (FIG. 10E for lesion volume, FIG. 11E for lesion surface area, FIG. 12E for lesion displacement, and FIG. 13G for lesion theoretical radius ratio). Further, a plot of the prediction error generated based on the posterior predictive distribution versus the observed values was generated (FIG. 10F for lesion volume, FIG. 11F for surface area, FIG. 12F for displacement, and FIG. 13H for theoretical radius ratio).

The statistical analysis showed that the average change in lesion volume for MS patients was 4.04 $mm^3$ lower than that for NSWMD patients (95% Confidence Interval (CI)=(-7.90, -0.45), Bayesian two-sided p<0.05). With a one standard deviation increase in age, the average lesion volume change for both MS and NSWMD patients increased by 1.95 $mm^3$ (95% CI=(0.17, 3.66), Bayesian two-sided p<0.05), with the average for MS patients being 0.49 $mm^3$ and the average for NSWMD patients being 4.53 $mm^3$ at that age. As such, MS patients' lesions tended to experience less volume growth compared to those of the NSWMD patients.

The average change in lesion surface area for MS patients was 3.72 $mm^2$ lower than that of NSWMD patients (95% CI=(-7.46, 0.052), Bayesian two-sided p=0.05). With a one standard deviation increase in age, the average change in lesion surface area for both MS and NSWMD patients increased by 1.72 $mm^2$ (95% CI=(0.06, 3.42), Bayesian two-sided p<0.05), with the average for MS patients being 0.5 $mm^2$ and the average for NSWMD patients being 4.22 $mm^2$. As such, MS patients' lesions tended to experience less surface area growth compared to those of the NSWMD patients (Bayesian two-sided p<0.05).

The difference in the average log of the median displacements between the MS and NSWMD groups was 0.37 (95% CI=(0.08, 0.66), Bayesian two-sided p=0.01), meaning for an MS patient of average age with an average duration between MRI scans the median displacement was 44.8% greater (95% CI=(9.33%, 93.5%)) than that of an NSWMD patient, controlling for age and duration between MRI scans. The log of the median displacement increased by 0.21 (95% CI=(0.08, 0.33), Bayesian two-sided p=0.0016) with a one standard deviation increase in the time elapsed between the different MRI timepoints, indicating a 23.4% increase in displacement relative to the original position (95% CI=(8.33%, 39.1%)).

For MS patients, the theoretical radius ratio was 39.94% greater than that of the NSWD patients at the first timepoint (95% CI=(17.29%, 66.23%), Bayesian two-sided p=0.0002) and 42.76% greater than that of the NSWMD patients at the second timepoint (95% CI=(19.72%, 68.51%), Bayesian two-sided p<0.0001), meaning that lesions from NSWMD patients tended to maintain a more spherical shape relative to those from MS patients. The theoretical radius ratio for both MS patients and NSWMD patients increased slightly between the first and second timepoints, but the change was not statistically significant (Bayesian two-sided p=0.291), indicating that the differences between the MS and NSWMD patients were maintained over time.

The estimated diagnosis-specific scale parameters for the lesion-specific random effects were $\hat{\sigma}_{NSWMD}$=0.77 (95% CI=(0.67, 0.89)) and $\hat{\sigma}_{MS}$=0.51 (95% CI=(0.40, 0.67)), which were significantly different (Bayesian two-sided p=0.006). The estimated shape parameters were $\hat{\sigma}_{NSWMD}$=12.14 (95% CI=(4.18, 25.02)) and $\hat{\sigma}_{MS}$=0.65 (95% CI=(-1.31, 2.62)), indicating that the MS and NSWMD groups had different shaper parameters (Bayesian two-sided p=0.0002), with the NSWMD group being more skewered in the lesion-specific random effects. While the overall variance of the lesion-specific random effects between the two diagnoses were not statically different (Bayesian two-sided p=0.239), the difference in the shape parameters between the two diagnoses demonstrated significantly less kurtosis for the MS patients (0.13, 95% CI=(-0.25, 0.61)) relative to the NSWMD patients (0.95, 95% CI=(0.81, 0.99), Bayesian two-sided p=0.0002).

Example 2

A leave-one-out cross-validation was performed to assess a threshold theoretical radius ratio and threshold proportion of lesions satisfying the deformation-based criteria that may permit accurate MS and NSWMD diagnoses. The data from Example 1 was separated into a test sample consisting of a single patient and a training sample consisting of the remainder of the patients. A logistic regression model was fit to the true diagnosis of a patient, with 0 corresponding to NSWMD and 1 corresponding to MS. The proportion of lesions greater than a given threshold were treated as the independent variable using the training sample. The probability of each of the patients in the training sample being diagnosed with MS was computed and the Area Under the Curve (AUC) was computed for all possible thresholds. The threshold with the maximum AUC was then used and the proportion of lesions greater than the threshold within each patient was computed. The logistic regression model was again fit and the probability that each patient was diagnosed with MS was computed for the training and testing sample. A Receiving Operator Characteristics (ROC) curve was then constructed to determine the probability cut-off which best differentiated the two diagnoses by choosing the probability cut-off which had the maximum summation of the sensitivity and specificity. Based on this probability cut-off, the predicted diagnosis was estimated for the patients in the training and testing samples. Lastly, the classification error for the training and testing samples were computed.

The results indicated that using a threshold theoretical radius ratio of 1.02507 and a threshold proportion of lesions satisfying the deformation-based criteria of 63%—meaning that an MS determination would be made when at least 63% of the lesions have a theoretical radius ratio at at least one time—yielded a sample accuracy of 94.1% (e.g., in-sample error of 5.9%) and an out-of-sample accuracy of 88% (e.g., out-of-sample error of 12%).

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A method of analyzing one or more lesions of a brain of a patient, the method comprising:
   for each of the lesion(s), from a first 3-dimensional (3D) representation of the lesion obtained from data taken at a first time and a second 3D representation of the lesion obtained from data taken at a second time that is after the first time, calculating one or more lesion characteristics that include:
      a change, from the first time to the second time, in the volume of the lesion;
      a change, from the first time to the second time, in the surface area of the lesion;
      a displacement of the lesion from the first time to the second time; and/or
      the theoretical radius ratio of the lesion at each of the first and second times;
   for each of the lesion(s), assessing whether one or more criteria are satisfied, the one or more criteria including:
      a volume-based criterion that is satisfied when the change in volume of the lesion is less than or equal to a threshold volume change less than or equal to 1.5 cubic millimeters ($mm^3$); and
   characterizing whether the patient has multiple sclerosis and/or the progression of multiple sclerosis in the patient based at least in part on: the calculation of the lesion characteristic(s) of each of the lesion(s) and the assessment of the one or more criteria for each of the lesion(s).

2. The method of claim 1, wherein the one or more criteria also includes:
   an area-based criterion that is satisfied when the change in the surface area of the lesion is less than or equal to a threshold surface area change;
   a displacement-based criterion that is satisfied when the displacement is greater than or equal to a threshold displacement; and
   a deformation-based criterion that is satisfied when the theoretical radius ratio of the lesion at each of the first and second times is greater than or equal to a threshold theoretical radius ratio.

3. The method of claim 1, comprising:
   determining for at least a majority of the lesion(s) that at least one of the one or more criteria is satisfied; and
   determining that the patient has multiple sclerosis.

4. The method of claim 1, wherein:
   the one or more criteria also includes:
      a displacement-based criterion that is satisfied when the displacement is greater than or equal to a threshold displacement and/or
      a deformation-based criterion that is satisfied when the theoretical radius ratio of the lesion at each of the first and second times is greater than or equal to a threshold theoretical radius ratio; and
   the threshold displacement and the threshold theoretical radius ratio are not determined based on the age of the patient.

5. The method of claim 1, wherein the one or more criteria also includes an area-based criterion that is satisfied when the change in the surface area of the lesion is less than or equal to a threshold surface area change.

6. The method of claim 1, wherein the data taken at the first time and the data taken at the second time each is a 3D magnetic resonance imaging (MRI) image of the brain of the patient.

7. The method of claim 1, wherein the time elapsed between the first and second times is between 6 months and 4 years.

8. A method of analyzing one or more lesions of a brain of a patient, the method comprising:
   for each of the lesion(s), from a first 3-dimensional (3D) representation of the lesion obtained from data taken at a first time and a second 3D representation of the lesion obtained from data taken at a second time that is after the first time, calculating one or more lesion characteristics that include:
      a change, from the first time to the second time, in the volume of the lesion;
      a change, from the first time to the second time, in the surface area of the lesion;
      a displacement of the lesion from the first time to the second time; and/or
      the theoretical radius ratio of the lesion at each of the first and second times;
   for each of the lesion(s), assessing whether one or more criteria are satisfied, the one or more criteria including:
      an area-based criterion that is satisfied when the change in the surface area of the lesion is less than or equal to a threshold surface area change less than or equal to 2.0 square millimeters ($mm^2$); and characterizing whether the patient has multiple sclerosis and/or the progression of multiple sclerosis in the patient based at least in part on: the calculation of the lesion characteristic(s) of each of the lesion(s) and the assessment of the one or more criteria for each of the lesion(s).

9. The method of claim 8, wherein the one or more criteria also includes:
a volume-based criterion that is satisfied when the change in volume of the lesion is less than or equal to a threshold volume change; and
the method further comprises determining the threshold volume change and/or the threshold surface area change based at least in part on the age of the patient.

10. The method of claim 8, wherein the one or more criteria also includes:
a volume-based criterion that is satisfied when the change in volume of the lesion is less than or equal to a threshold volume change;
a displacement-based criterion that is satisfied when the displacement is greater than or equal to a threshold displacement; and
a deformation-based criterion that is satisfied when the theoretical radius ratio of the lesion at each of the first and second times is greater than or equal to a threshold theoretical radius ratio.

11. The method of claim 8, comprising:
determining for at least a majority of the lesion(s) that at least one of the one or more criteria is satisfied; and
determining that the patient has multiple sclerosis.

12. The method of claim 8, wherein:
the one or more criteria also includes:
a displacement-based criterion that is satisfied when the displacement is greater than or equal to a threshold displacement; and/or
a deformation-based criterion that is satisfied when the theoretical radius ratio of the lesion at each of the first and second times is greater than or equal to a threshold theoretical radius ratio; and
the threshold displacement and the threshold theoretical radius ratio are not determined based on the age of the patient.

13. A system for analyzing one or more lesions of a brain of a patient, the system comprising one or more processors configured to:
for each of the lesion(s), from a first 3-dimensional (3D) representation of the lesion obtained from data taken at a first time and a second 3D representation of the lesion obtained from data taken at a second time that is after the first time, calculate one or more lesion characteristics that include:
a change, from the first time to the second time, in the volume of the lesion;
a change, from the first time to the second time, in the surface area of the lesion;
a displacement of the lesion from the first time to the second time; and/or
the theoretical radius ratio of the lesion at each of the first and second times;
for each of the lesion(s), assess whether one or more criteria are satisfied, the one or more criteria including:
a volume-based criterion that is satisfied when the change in volume of the lesion is less than or equal to a threshold volume change less than or equal to 1.5 cubic millimeters ($mm^3$); and
characterize whether the patient has multiple sclerosis and/or the progression of multiple sclerosis in the patient based at least in part on: the calculation of the lesion characteristic(s) of each of the lesion(s) and the assessment of the one or more criteria for each of the lesion(s).

14. The system of claim 13, wherein the one or more criteria also includes:
an area-based criterion that is satisfied when the change in the surface area of the lesion is less than or equal to a threshold surface area change;
a displacement-based criterion that is satisfied when the displacement is greater than or equal to a threshold displacement; and
a deformation-based criterion that is satisfied when the theoretical radius ratio of the lesion at each of the first and second times is greater than or equal to a threshold theoretical radius ratio.

15. The system of claim 13, wherein:
one or more criteria also includes:
a displacement-based criterion that is satisfied when the displacement is greater than or equal to a threshold displacement and/or a the deformation-based criterion that is satisfied when the theoretical radius ratio of the lesion at each of the first and second times is greater than or equal to a threshold theoretical radius ratio; and
the processor(s) are configured to assess whether the displacement-based criterion and/or the deformation-based criterion are satisfied without determining the threshold displacement and/or the threshold theoretical radius ratio based on the age of the patient.

16. The system of claim 13, wherein the data taken at the first time and the data taken at the second time each is a 3D magnetic resonance imaging (MRI) image of the brain of the patient.

17. A system for analyzing one or more lesions of a brain of a patient, the system comprising one or more processors configured to:
for each of the lesion(s), from a first 3-dimensional (3D) representation of the lesion obtained from data taken at a first time and a second 3D representation of the lesion obtained from data taken at a second time that is after the first time, calculate one or more lesion characteristics that include:
a change, from the first time to the second time, in the volume of the lesion;
a change, from the first time to the second time, in the surface area of the lesion;
a displacement of the lesion from the first time to the second time; and/or
the theoretical radius ratio of the lesion at each of the first and second times;
for each of the lesion(s), assess whether one or more criteria are satisfied, the one or more criteria including:
an area-based criterion that is satisfied when the change in the surface area of the lesion is less than or equal to a threshold surface area change less than or equal to 2.0 square millimeters ($mm^2$); and
characterize whether the patient has multiple sclerosis and/or the progression of multiple sclerosis in the patient based at least in part on: the calculation of the lesion characteristic(s) of each of the lesion(s) and the assessment of the one or more criteria for each of the lesion(s).

18. The system of claim 17, wherein the one or more criteria also includes:
a volume-based criterion that is satisfied when the change in volume of the lesion is less than or equal to a threshold volume change; and the processor(s) are configured to determine the threshold volume change and/or the threshold surface area change based at least in part on the age of the patient.

19. The system of claim 17, wherein the one or more criteria also includes:
   a displacement-based criterion that is satisfied when the displacement is greater than or equal to a threshold displacement; and/or a deformation-based criterion that is satisfied when the theoretical radius ratio of the lesion at each of the first and second times is greater than or equal to a threshold theoretical radius ratio; and
   the processor(s) are configured to assess whether the displacement-based criterion and/or the deformation-based criterion are satisfied without determining the threshold displacement and/or the threshold theoretical radius ratio based on the age of the patient.

20. The system of claim 17, wherein the one or more criteria also includes:
   a volume-based criterion that is satisfied when the change in volume of the lesion is less than or equal to a threshold volume change;
   a displacement-based criterion that is satisfied when the displacement is greater than or equal to a threshold displacement; and
   a deformation-based criterion that is satisfied when the theoretical radius ratio of the lesion at each of the first and second times is greater than or equal to a threshold theoretical radius ratio.

21. The system of claim 17, wherein the data taken at the first time and the data taken at the second time each is a 3D magnetic resonance imaging (MRI) image of the brain of the patient.

* * * * *